(12) United States Patent
Mansouri et al.

(10) Patent No.: US 9,904,890 B2
(45) Date of Patent: Feb. 27, 2018

(54) DETECTING A TRANSIENT ERROR IN A BODY FLUID SAMPLE

(71) Applicant: Instrumentation Laboratory Company, Bedford, MA (US)

(72) Inventors: Sohrab Mansouri, Sudbury, MA (US); Jose Maria Cervera, Arlington, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 415 days.

(21) Appl. No.: 14/657,254

(22) Filed: Mar. 13, 2015

(65) Prior Publication Data

US 2016/0267389 A1    Sep. 15, 2016

(51) Int. Cl.
*G06N 7/00*     (2006.01)
*G06F 17/18*    (2006.01)
*G01N 35/00*    (2006.01)

(52) U.S. Cl.
CPC ......... *G06N 7/00* (2013.01); *G01N 35/00613* (2013.01); *G06F 17/18* (2013.01)

(58) Field of Classification Search
None
See application file for complete search history.

(56) References Cited

U.S. PATENT DOCUMENTS

| 5,112,455 A | 5/1992 | Cozzette et al. |
| 5,890,489 A | 4/1999 | Elden |
| 6,424,847 B1 | 7/2002 | Mastrototaro et al. |
| 6,615,064 B1 | 9/2003 | Aldrich |
| 6,652,720 B1 | 11/2003 | Mansouri et al. |
| 7,022,219 B2 | 4/2006 | Mansouri et al. |
| 7,087,149 B1 | 8/2006 | Muguruma et al. |
| 7,632,672 B2 | 12/2009 | Pamidi et al. |

(Continued)

FOREIGN PATENT DOCUMENTS

WO    2001/33195    5/2001

OTHER PUBLICATIONS

Bronshtein, et al. Handbook of Mathematics, Fifth edition. (Springer-Verlag, 2007), pp. 379-392.

(Continued)

*Primary Examiner* — Alan Chen
(74) *Attorney, Agent, or Firm* — Burns & Levinson, LLP

(57) ABSTRACT

An approach for detecting a transient error in a body fluid sample based on the shape of a response curve of a sensor is provided. The response curve is represented by an equation including at least one coefficient describing a curvature or slope of the response curve. The approach includes comparing the coefficient to a range of coefficients which includes coefficients of response curves corresponding to known analyte concentrations. The approach further includes detecting a transient error based on the comparison. In some examples of the approach, the comparison and detection are performed by a processing transient error detector executing computer readable instructions embodied in a non-transitory computer-readable medium. Other examples of the approach determine a concentration of the analyte based on the equation. Advantageously, various examples of the approach can expedite detection of transient errors at the time of measuring and before reporting sample result.

19 Claims, 19 Drawing Sheets

(56) References Cited

U.S. PATENT DOCUMENTS

| | | | |
|---|---|---|---|
| 7,972,280 | B2 | 7/2011 | Azer et al. |
| 8,042,073 | B1 | 10/2011 | Nnaji |
| 8,112,375 | B2 | 2/2012 | Pav |
| 8,226,555 | B2 | 7/2012 | Say et al. |
| 8,231,532 | B2 | 7/2012 | Say et al. |
| 8,231,534 | B2 | 7/2012 | Habu et al. |
| 8,560,251 | B2 | 10/2013 | Mansouri et al. |
| 2002/0053523 | A1 | 5/2002 | Liamos et al. |
| 2005/0130249 | A1 | 6/2005 | Parris et al. |
| 2005/0203360 | A1* | 9/2005 | Brauker ............... A61B 5/1468 600/345 |
| 2006/0167351 | A1 | 7/2006 | Isaacson et al. |
| 2007/0136834 | A1 | 6/2007 | Greenbaum et al. |
| 2008/0102441 | A1 | 5/2008 | Chen et al. |
| 2008/0114549 | A1 | 5/2008 | Schafer et al. |
| 2008/0215254 | A1 | 9/2008 | Leiner et al. |
| 2009/0194432 | A1 | 8/2009 | Deng |
| 2010/0049022 | A1 | 2/2010 | Parris et al. |
| 2010/0168535 | A1 | 7/2010 | Robinson et al. |
| 2012/0209566 | A1 | 8/2012 | Idiart |
| 2012/0262298 | A1* | 10/2012 | Bohm ................ G01N 27/3274 340/604 |
| 2013/0046478 | A1 | 2/2013 | Mansouri et al. |
| 2013/0046483 | A1 | 2/2013 | Mansouri et al. |
| 2013/0245401 | A1* | 9/2013 | Estes .................. A61B 5/14532 600/309 |
| 2014/0100794 | A1 | 4/2014 | Mansouri et al. |
| 2016/0033340 | A1* | 2/2016 | Todd .................... G01K 15/005 374/1 |

OTHER PUBLICATIONS

Chen, Prof. Ray-Bing,—Ch. 6—Kaohsiung University: Regression Analysis: Fall 2008 (Powerpoint files) pp. 1-33.

Looking at Data-Relationships cautions about correlation and regression. Available online: https://www.stt.msu.edu/Academics/ClassPages/uploads/FS12/421-I/Lecture_ch2_part4.pdf.2009.

Martin, David W.—Teaching Leverage, Outliers, and Influential Observations in Introductory Statistics Courses: submitted to JSE 2012. pp. 1-19. Also available online at www.davidson.edu/cros/Documents/.../ACAD_ECO_jse.pdf.

McDonald, J.H.—Handbook of Biological Statistics. (2008). Excerpt of pp. 205-210.

Motulsky, H. J.—PRISM 4 Statistics Guide. (GraphPad Software, Inc. San Diego, CA 2005). 3 excerpted pages, with 2 pages of front matter.

Motulsky, H. J.—PRISM 4 Statistics Guide. (GraphPad Software, Inc. San Diego, CA 2005). Excerpt of pp. 25-28.

Patent Cooperation Treaty, International Preliminary Report on Patentability, International Application No. PCT/US2012/051049, dated Feb. 18, 2014; 5 pages.

Patent Cooperation Treaty, International Preliminary Report on Patentability, International Application No. PCT/US2012/051140, dated Feb. 18, 2014; 7 pages.

Patent Cooperation Treaty, International Search Report (ISR) & Written Opinion of the ISR, International Application No. PCT/US2012/051140, dated Nov. 2, 2012; 13 pages.

Patent Cooperation Treaty, International Search Report (ISR) & Written Opinion of the ISR, International Application No. PCT/US2012/051049, dated Nov. 2, 2012; 9 pages.

Walfish, Steven—A Review of Statistical Outlier Methods: Nov. 2, 2006; Pharmaceutical Technology, pp. 1-5. Also available online: http://www.pharmtech.com/pharmtech/content/printContentPopup.jsp?id=384716.

Wang, J.—Glucose Biosensors: 40 Years of Advances and Challenges. Electroanalysis 13, 983-988 (2001).

Patent Cooperation Treaty, International Search Report (ISR) & Written Opinion of the ISR, International Application No. PCT/US2016/020185, dated Jun. 13, 2016; 15 pages.

International Bureau of WIPO, International Preliminary Report on Patentability (IPRP), International Application No. PCT/US2016/020185, dated Sep. 28, 2017, 11 pages.

* cited by examiner

DETECTING A TRANSIENT ERROR IN A BODY FLUID SAMPLE

FIELD OF THE INVENTION

The present invention relates generally to a quality assurance program for detecting errors during a testing process. More specifically, the present invention relates to an approach for detecting a transient error in a body fluid sample that is based on the shape of a response curve of a sensor.

BACKGROUND OF THE INVENTION

Since primary users of point-of-care (POC) devices are health professionals from a non-laboratory background, POC clinical analyzers should be designed for ease of use, low maintenance, and well-controlled. A key requirement in developing such a system is having a total quality assurance (QA) program with the capability to detect errors during each stage of the testing process, that is, pre-analytical, analytical and post analytical.

The Intelligent Quality Management (iQM) in the GEM Premier line of automated clinical analyzers for measurement of blood gases, electrolytes, metabolites and CO-Oximetry produced by Instrumentation Laboratory of Bedford, Mass. is an example of such comprehensive QA program. The primary method of error detection is based on monitoring sensor drift by the process control solutions and using drift limit as control parameter for detecting errors. The source of error, such as interfering substances and blood clots, is detected through identifying specific known drift patterns.

SUMMARY OF THE INVENTION

The present invention overcomes the drawbacks of prior art devices and methods; and is directed towards an approach for detecting a transient error in a body fluid sample based on the shape of a response curve of a sensor. According to various embodiments described herein, the present invention describes an application of a new sensor response pattern check during sample measurement for enhancing error detection capabilities. Some examples of the approach are based on fitting sensor response outputs to a logarithmic polynomial function for determining the fit coefficients. Magnitude of the fit coefficients is used as indicator of the sample response shape for detecting transient errors in a body fluid sample.

In one aspect, a system for detecting a transient error in a body fluid sample includes memory having computer executable instructions thereupon and at least one interface for receiving an equation representing a response curve of a sensor and for determining a concentration of an analyte in a body fluid sample. The equation includes at least one coefficient describing any one of a curvature of the response curve and a slope of the response curve. The system further includes a transient error detector coupled to the memory and the at least one interface. The transient error detector is configured to execute the instructions and compare the at least one coefficient to a range of coefficients. The range of coefficients includes coefficients of response curves corresponding to known concentrations of the analyte. The transient error detector detects a transient error in the body fluid sample based on the comparison.

In other examples of the system, the equation representing the response curve is any one of logarithmic equation and quadratic equation.

In some examples of the system, the range of coefficients for a given concentration of analyte includes a mean coefficient determined from a mean of coefficients of response curves corresponding to the given concentration of analyte. The range of coefficients further includes a lower limit defined by a negative number of standard deviations from the mean coefficient and an upper limit defined by a positive number of standard deviations from the mean coefficient.

In another aspect, a tangible non-transitory computer-readable storage medium having computer readable instructions stored therein for detecting a transient error in a body fluid sample is provided. When the instructions are executed by one or more processors that are provided with an equation representing a response curve of a sensor and for determining a concentration of an analyte in a body fluid sample, and the equation including at least one coefficient describing any one of a curvature of the response curve and a slope of the response curve, the one or more processors are caused to compare the at least one coefficient to a range of coefficients, the range of coefficients including coefficients of response curves corresponding to known concentrations of the analyte. The one or more processors are further caused to detect a transient error in the body fluid sample based on the comparison.

In other examples of the tangible non-transitory computer-readable storage medium, the equation representing the response curve is any one of logarithmic equation and quadratic equation.

In some examples of the tangible non-transitory computer-readable storage medium, the range of coefficients for a given concentration of analyte includes a mean coefficient determined from a mean of coefficients of response curves corresponding to the given concentration of analyte. The range of coefficients further includes a lower limit defined by a negative number of standard deviations from the mean coefficient and an upper limit defined by a positive number of standard deviations from the mean coefficient.

In yet another aspect, a method for detecting a transient error in a body fluid sample taken from a patient includes, in a clinical analyzer provided with an equation representing a response curve of a sensor and for determining a concentration of an analyte in a body fluid sample, and the equation including at least one coefficient describing any one of a curvature of the response curve and a slope of the response curve, comparing the at least one coefficient to a range of coefficients, the range of coefficients including coefficients of response curves corresponding to known concentrations of the analyte. The method further includes detecting a transient error in the body fluid sample based on the comparison. The comparison and the detection are performed by a processing transient error detector executing computer readable instructions embodied in a non-transitory computer-readable medium.

In some examples of the method, the equation representing the response curve is any one of logarithmic equation and quadratic equation.

In other examples of the method, the equation is associated with the analyte being sensed by the sensor.

In some examples of the method, comparing includes comparing a coefficient describing the curvature of the response curve to the range of coefficients and comparing a coefficient describing the slope of the response curve to a second range of coefficients different than the range of coefficients. In these examples, detecting includes detecting the transient error in the body fluid sample based on the comparison of the coefficient describing the curvature of the response curve and the comparison of the coefficient describing the slope of the response curve.

In other examples of the method, the range of coefficients for a given concentration of analyte includes a mean coefficient determined from a mean of coefficients of response curves corresponding to the given concentration of analyte. The range of coefficients further includes a lower limit defined by a negative number of standard deviations from the mean coefficient and an upper limit defined by a positive number of standard deviations from the mean coefficient.

In some examples of the method, an absolute value of the negative number of standard deviations from the mean coefficient and an absolute value of the positive number of standard deviations from the mean coefficient are different.

In other examples of the method, the lower limit and the upper limit of the range of coefficients are invariant to changes in concentration of the analyte.

In some examples of the method, at least one of the lower limit and the upper limit of the range of coefficients varies with changes in concentration of the analyte.

Another example of the method further includes revising the range of coefficients based on the coefficient of the response curve corresponding to the concentration of the analyte in the body fluid sample.

In some examples of the method, the known concentrations of the analyte are determined from at least one of previously collected body fluid samples and standardized solutions.

In other examples of the method, the range of coefficients depends on a matrix of the body fluid sample.

Another example of the method further includes based on a result of the detection, determining the concentration of the analyte in the body fluid sample based on the equation.

Yet another example of the method further includes determining the concentration of the analyte in the body fluid sample based the equation. In this example, detecting the transient error includes detecting the transient error in the determined concentration of the analyte based on the comparison.

Still yet another example of the method further includes based on the detection, reporting to a user of the analyzer that a transient error is detected in the body fluid sample.

In some examples, reporting includes to providing a visual alarm, an audible alarm or a combination thereof to the user.

Another example of the method further includes based on the detection, stopping a sample measurement process including determining the concentration of the analyte.

Yet another example of the method further includes based on the detection, reporting to a user of the analyzer that the body fluid sample may be compromised by a transient error; and continuing a sample measurement process including determining the concentration of the analyte.

BRIEF DESCRIPTION OF THE DRAWINGS

These embodiments and other aspects of this invention will be readily apparent from the detailed description below and the appended drawings, which are meant to illustrate and not to limit the invention, and in which.

DESCRIPTION

The present invention will be more completely understood through the following description, which should be read in conjunction with the attached drawings. In this description, like numbers refer to similar elements within various embodiments of the present invention. Within this description, the claimed invention will be explained with respect to embodiments. The skilled artisan will readily appreciate that the methods and systems described herein are merely exemplary and that variations can be made without departing from the spirit and scope of the invention.

Figure 1A:
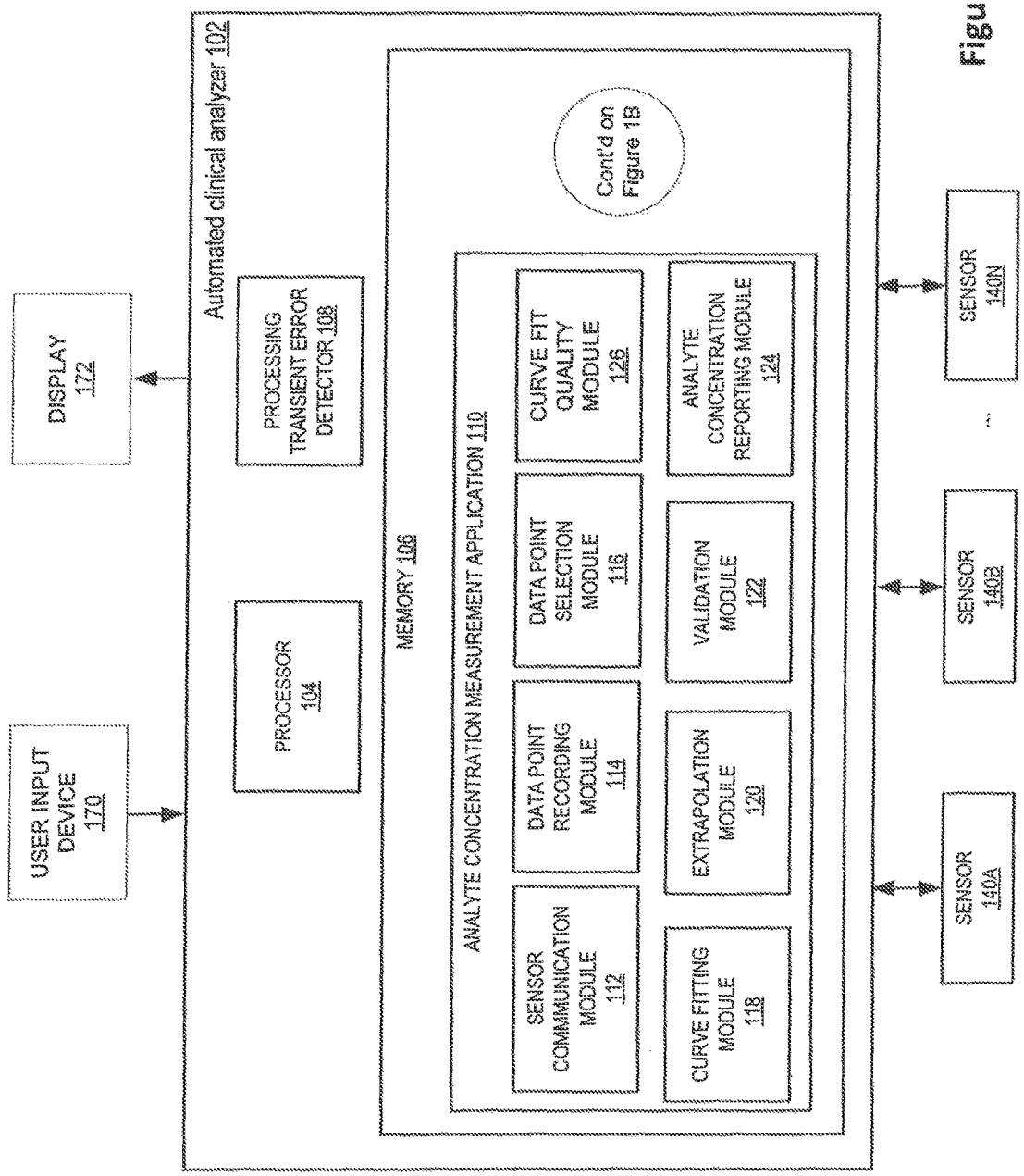
FIGS. 1a and 1b show an exemplary block diagram of an automated clinical analyzer according to one embodiment of the invention.
Figure 1B:
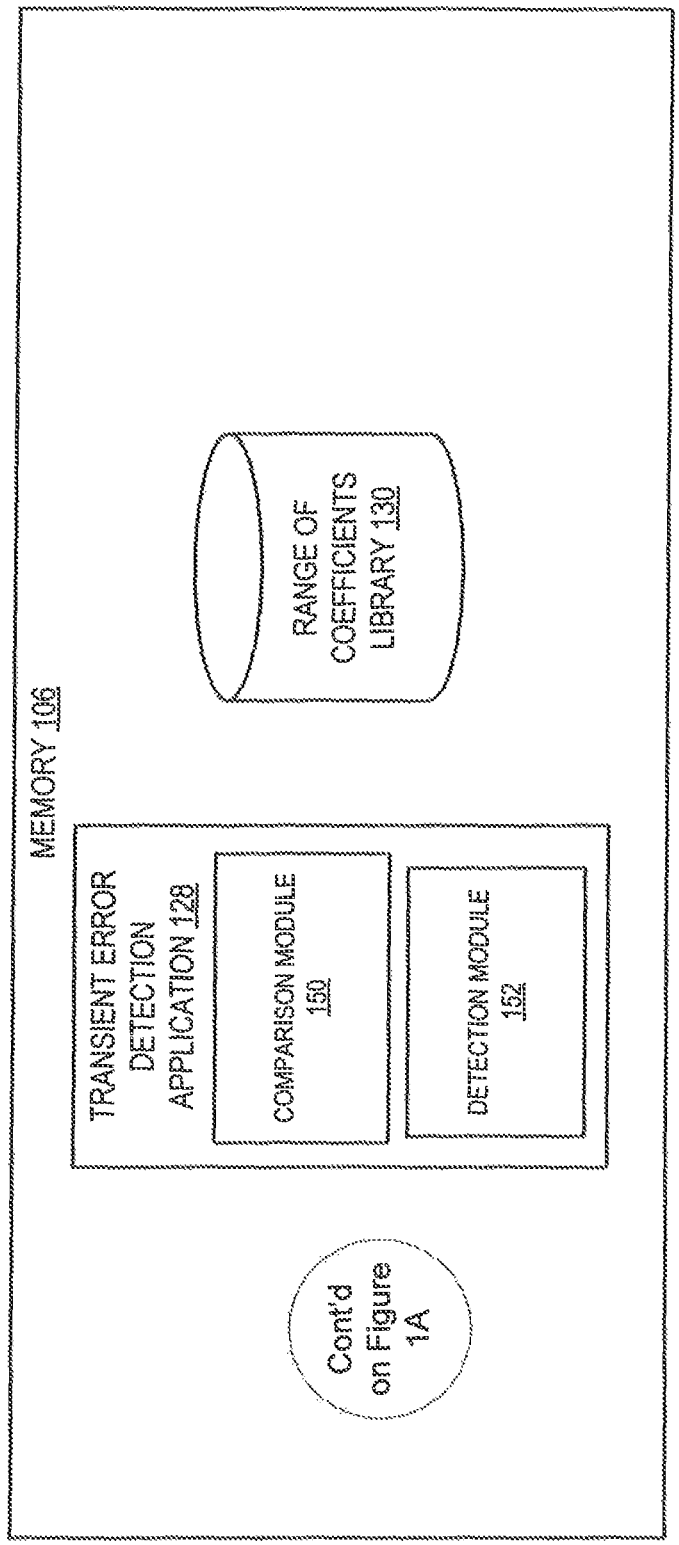

FIGS. 1a and 1b show an example of an automated clinical analyzer 102 for measuring analytes, such as potassium, chloride, sodium, glucose, lactate, creatinine, creatine, urea, O2, CO2, and the like, in a body fluid sample (e.g., whole blood) taken from a patient. The automated clinical analyzer is generally configured to communicate with one or more sensors 140A-N, generally referred to hereinafter as sensors 140. In various examples of the automated clinical analyzer, the sensors 140 may be electrochemical sensors that generate voltmetric or amperometric signals in response to being exposed to analytes. In various examples, a first sensor 140A may be responsive to a first analyte within a body fluid sample, a second sensor 140B may be responsive to a second analyte within the body fluid sample, and an nth sensor 140N may be responsive to an nth analyte within the body fluid sample, and so forth. Further details regarding the sensors 140 are provided below.

An operator (e.g., a health professional) loads a body fluid sample into the automated clinical analyzer 102 and starts a sample measurement process (analysis) for a particular analyte. In particular, the operation uses a user interface 170, such as a keyboard and/or mouse, communicatively coupled to the automated clinical analyzer 102 to start the process. In analyzing the body fluid sample for the analyte, the automated clinical analyzer 102 can detect transient errors in the body fluid sample. Transient errors, such as an air bubble, a blood clot or other interfering substance in the body fluid sample, can lead to errors in sample measurements, for example, an erroneous analyte concentration. An approach to detecting transient errors in the body fluid sample that is based on the shape of a response curve of the sensor is described below.

The sensor 140 generates signals in response to sensing the analyte in the body fluid sample. The generated signals can be used to create the response curve of the sensor (described in more detail below). The response curve can be mathematically represented by an equation including logarithmic and quadratic equations. Examples of the equation can include a coefficient describing a curvature of the response curve, a coefficient describing the slope of the response curve or both.

When the equation coefficient(s) falls inside a range of coefficients, the response curve is defined as having a "good" shape. When the equation coefficient(s) falls outside a range of coefficients, the response curve is defined as having a "bad" shape. The automated clinical analyzer 102 determines there is no transient error in the body fluid sample when the response curve of the sensor 140 has a good shape. The automated clinical analyzer 102 determines there is transient error in the body fluid sample when the response curve of the sensor 140 has a bad shape. The automated clinical analyzer 102 notifies the operator whether there is a transient error in the body fluid sample. For example, the notification is presented to the operator using a display 172 communicatively coupled to the automated clinical analyzer 102.

In analyzing the analyte, the automated clinical analyzer 102 can also determine the concentration of the analyte based on the signals generated by the sensor 140. In a convenient example, the concentration of the analyte is determined according an approach for increasing sample throughput, as described below in greater detail. The automated clinical analyzer 102 notifies the operator of the concentration of the analyte, for example, through the display 172. In some cases, when the automated clinical analyzer 102 detects a transient error in the body fluid sample, the automated clinical analyzer 102 stops the sample measurement process and does not determine the concentration of the analyte.

Continuing with FIGS. 1a and 1b, the automated clinical analyzer 102 includes a processor 104, a memory 106, a processing transient error detector 108, an analyte concentration measurement application 110, a transient error detection application 128, and a range of coefficients library 130. In some examples of the automated clinical analyzer 102, the processor 104 includes the processing transient error detector 108. The memory 106 stores the analyte concentration measurement application 110, the transient error detection application 128, and the range of coefficients library 130. Operation of the automated clinical analyzer 102 is described below in greater detail starting with a discussion of the processing transient error detector 108 and the transient error detection application 128. The analyte concentration measurement application 110 is discussed in the second half of the disclosure.

The processing transient error detector or simply "transient error detector" 108 runs the transient error detection application 128. As shown, an example of the transient error detection application 128 includes a comparison module 150 and a detection module 152 configured to perform specific functions or tasks in order to detect a transient error in a body fluid sample that is based on the shape of a response curve of a sensor. Other examples include more or fewer modules. Operation of the transient error detector 108 is described below with reference to the functional block diagram of FIG. 9 and the flow diagram of FIG. 10.

Figure 9:
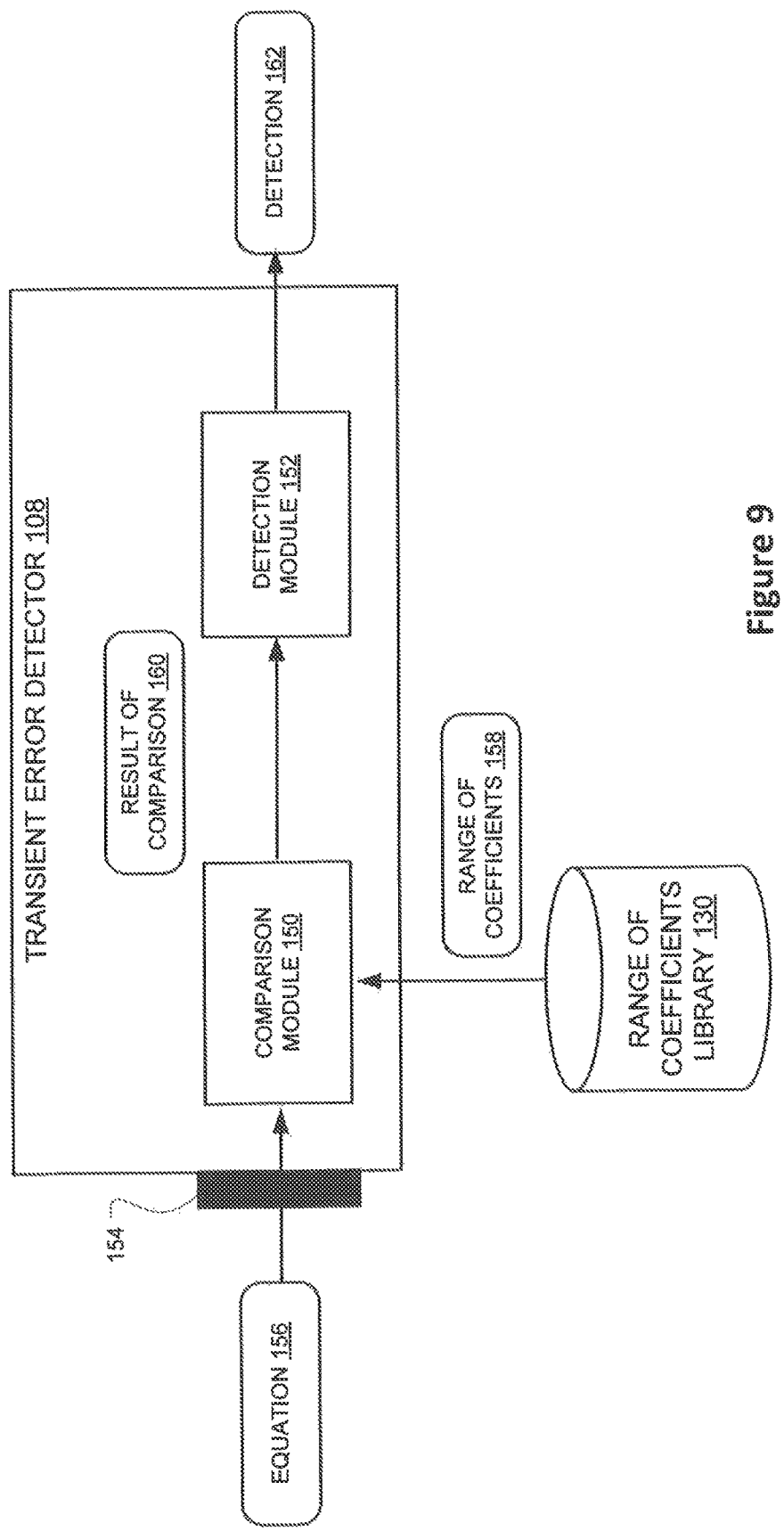
FIG. 9 shows an exemplary block diagram of a processing transient error detector according to one embodiment of the invention.

FIG. 9 shows an example of the transient error detector 108. The transient error detector 108 includes the comparison module 150 and the detection module 152 communicatively coupled as shown. The transient error detector 108 further includes an interface 154 for receiving equations 156 representing sensor response curves. In some use cases, the interface 154 receives the equations 156 as they are determined by the analyte concentration measurement application 110. Advantageously, this enables real or near real-time detection of transient errors in body fluid samples. For example, the automated clinical analyzer 102 notifies the operator of a detected transient error during the sample measurement process. In other use cases, the interface 154 receives equations previously determined. Asynchronous detection of transient errors can be beneficial when batch (i.e., more than one) processing of samples is desirable. For example, equations determined by a separate instrument are sent to the automated clinical analyzer 102 to detect transient errors. As shown, the range of coefficients library provides a range of coefficients 158 for a particular analyte used to detect a transient error in the body fluid sample.

Figure 10:
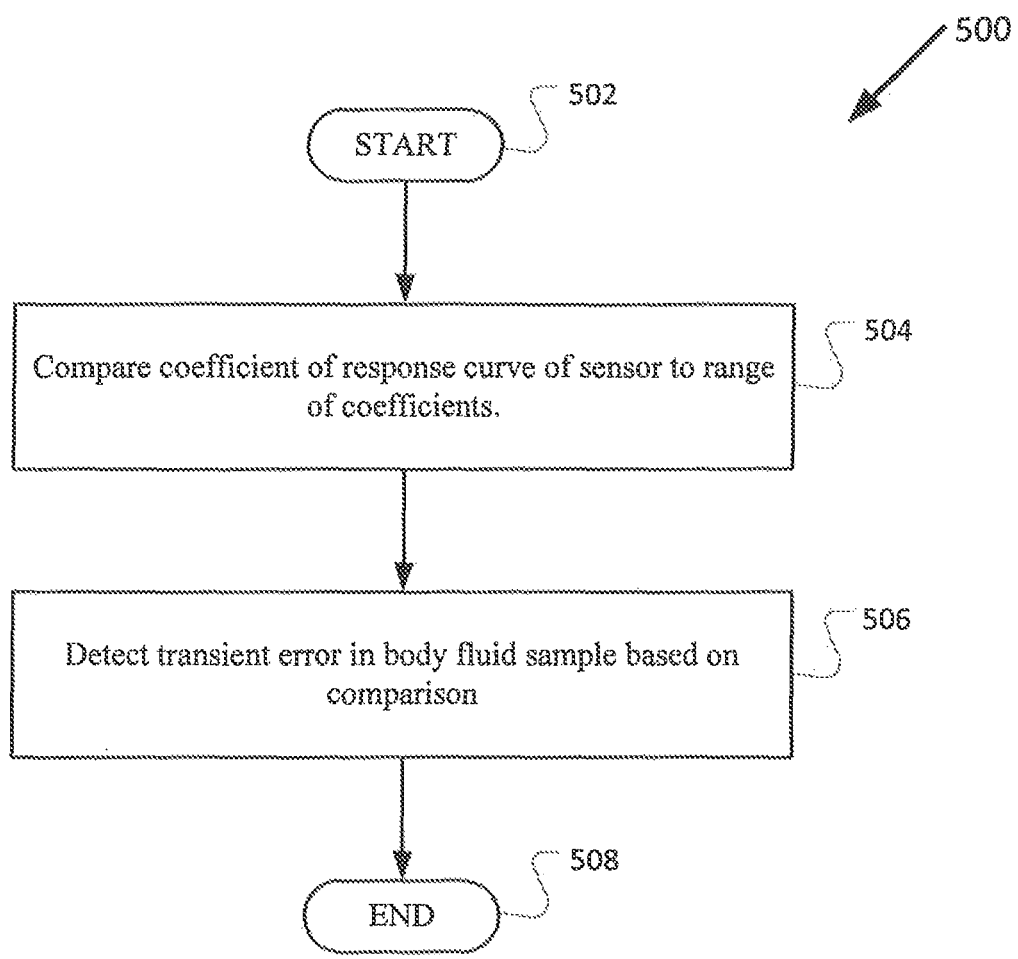
FIG. 10 is exemplary logical flow diagram for detecting a transient error in a body fluid sample according to one embodiment of the invention.

FIG. 10 shows an example routine 500 for detecting transit errors in body fluid samples. The routine 500 starts at operation 502 with the comparison module 150 being provided with the equation 156 representing a response curve. The response curve is for a sensor sensing a particular analyte in a body fluid sample and for ease of reference is called a "response curve under test." The equation 156 may include a coefficient describing a curvature of the response curve under test, a coefficient describing a slope of the response curve under test or both.

At operation 504, a convenient example of the comparison module 150 compares the coefficient (describing curvature or slope) against the range of coefficients 158. The comparison operation 504 is described in greater detail with reference to FIG. 11a. The figure shows a graphical representation of an example range of coefficients 602, specifically, for a sensor sensing oxygen in the body fluid sample. Coefficient values are on shown on the horizontal axis of the graph and oxygen concentration values are on shown on the vertical axis of the graph. The range of coefficients 602 includes a lower limit 604 and an upper limit 606 that both vary with a changing in oxygen concentration.

As shown, point A has a coefficient value below the lower limit 604 and is outside the range of coefficients 602. Point B has a coefficient value above the upper limit 606 and is outside the range of coefficients 602. Because point A and point B are outside the range of coefficients 602 the comparison module 150 determines that the response curve under test having a coefficient value of either these points has a bad shape. Point C has a coefficient value between the lower limit 604 and the upper limit 606, and is within the range of coefficients 602. Because point C is within the range of coefficients 602 the comparison module 150 determines that the response curve under test having a coefficient value of point C has a good shape.

Returning to FIGS. 9 and 10, at operation 506, based on a result of the comparison 160 (i.e., the response curve under test has a good shape or has a bad shape), the detection module 152 detects whether there is a transient error in the body fluid sample and returns a detection 162 (i.e., transient error detected or no transient error detected). A convenient example of the detection module 152 identifies no transient error in the body fluid sample when the coefficient of the response curve under test is within the range of coefficient. The detection module 152 identifies there is a transient error in the body fluid sample when the coefficient of the response curve under test is outside the range of coefficient. The routine 500 end at operation 508 with the detection module 152 returning a detection 162 (i.e., transient error detected or no transient error detected).

The usefulness of the transient error detector 108 can be further enhanced by considering two or more coefficients when determining whether the response curve under test has a good shape or bad shape. In a convenient example of the transient error detector 108, the comparison module 150 compares a coefficient describing the curvature of the response curve under test to a first range of coefficients and compares a coefficient describing the slope of the response curve under test to a second range of coefficients. The detection module 152 determines whether there is a transient error in the body fluid sample based on the result of comparing the curvature (first comparison) and the result of comparing the slope (second comparison). The detection module 152 combines the results, for example by weighting them equally or differently. Including additional determinants or factors in the detection process is advantageous because it enables transient errors to be detected with greater granularity.

Upon detecting the transient error in the body fluid sample, a convenient example of the automated clinical analyzer 102 terminates the sample measurement process and reports to the technician (operator) by means of a visual and/or audible alarm (e.g., through the monitor 172 of FIG. 1). The alarm informs the technician that the transient error detector 108 has detected a transient error for that body fluid sample for that analyte. Another example of the automated clinical analyzer 102 continues with the sample measurement process and notifies the technician (operator) by means of a visual and/or audible alarm (e.g., through the monitor 172 of FIG. 1) that the body fluid sample result for that analyte is potentially compromised by a transient error.

Upon determining there is no transient error in the body fluid sample, another convenient example of the automated clinical analyzer 102 determines the concentration of the analyte in the body fluid sample based on the equation 156, as described in greater detail below. Advantageously, this can save on processing time and resources by only computing the concentration when there is no transient error that could cause the concentration to be computed incorrectly.

Another example of the automated clinical analyzer 102 determines both the concentration of the analyte in the body fluid sample based on the equation 156 (described in greater detail below) and detects whether there is a transient error in the body fluid sample. Advantageously, this example of the automated clinical analyzer 102 identifies whether there is transient error in the determined concentration improving the usefulness automated clinical analyzer 102.

An example of a procedure for creating a range of coefficients from previously collected samples is now described with reference to FIGS. 11a through 11c. The previously collected samples include body fluid samples and standardized aqueous solutions of a particular analyte at varied concentrations. The analyte concentration of each of the previously collected samples is measured. The sample measurements are then verified to be within an allowable analyte accuracy limit. It should be readily apparent that the verifying can be performed according to any one of a number of well-known techniques, for example, testing the same sample using a number of identical analyzers. Examples of the procedure are not limited to any one particular verification technique.

Response curves generated while measuring analyte concentrations of the previously collected samples are analyzed, including determining equations representing the response curves. For equation coefficients associated with previously collected samples having similar or the same measured analyte concentration (e.g., samples having a concentration plus or minus 5 percentage are considered similar), a mean coefficient is determined. The mean coefficients for different measured analyte concentrations are used to determine a lower limit and an upper limit of a response curve.

Figure 11A:
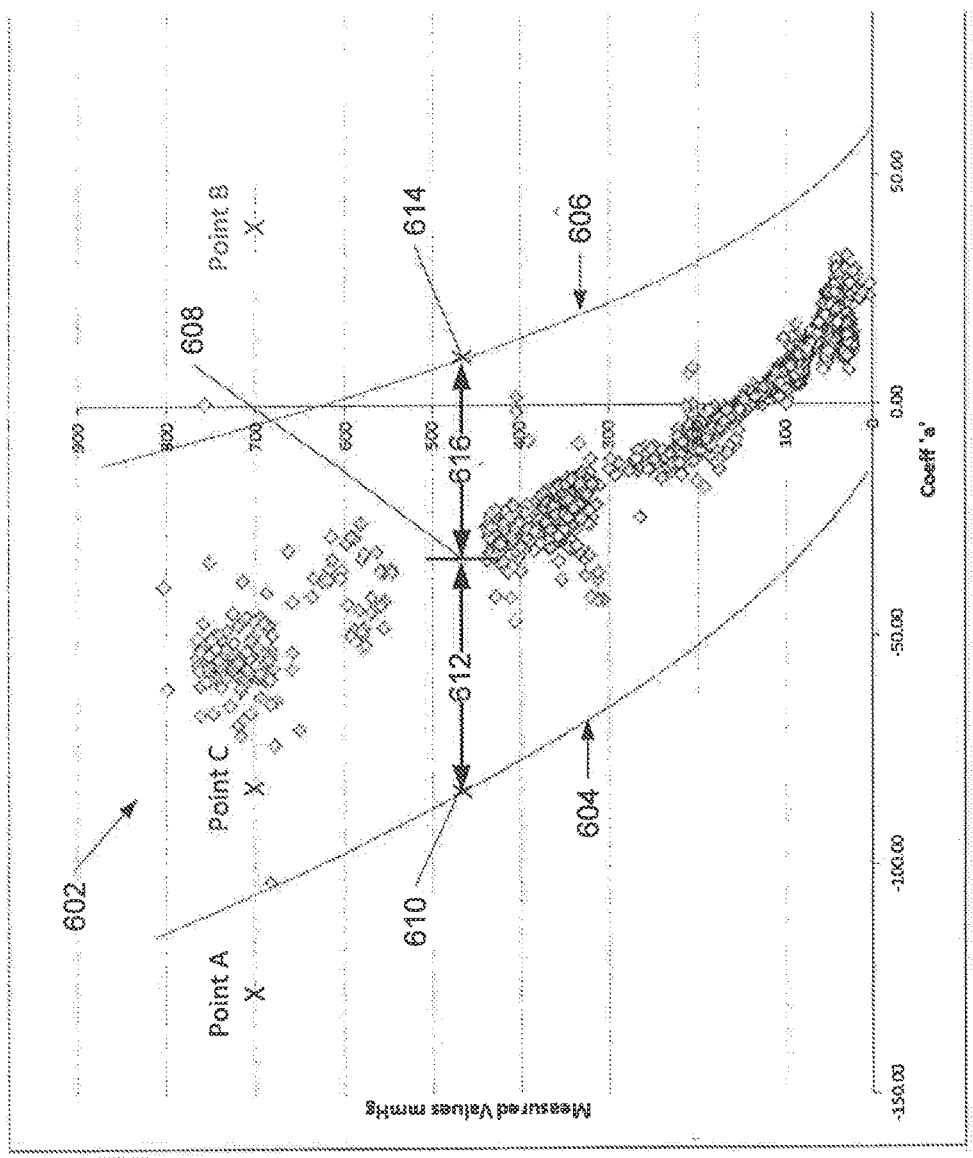
FIGS. 11a-c show an exemplary graphical representations of range of coefficients created from previously collected samples according to one embodiment of the invention.
Figure 11B:
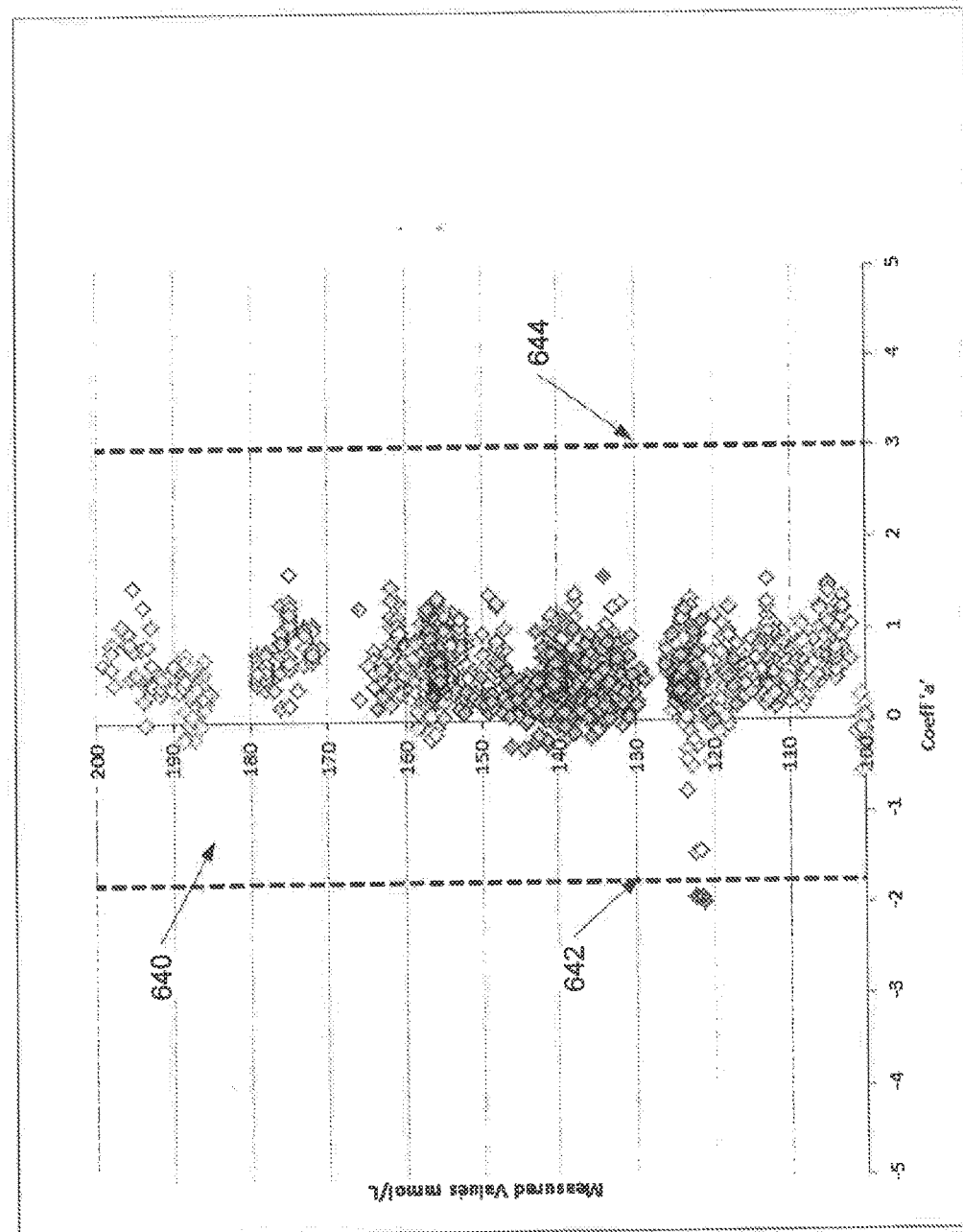
Figure 11C:
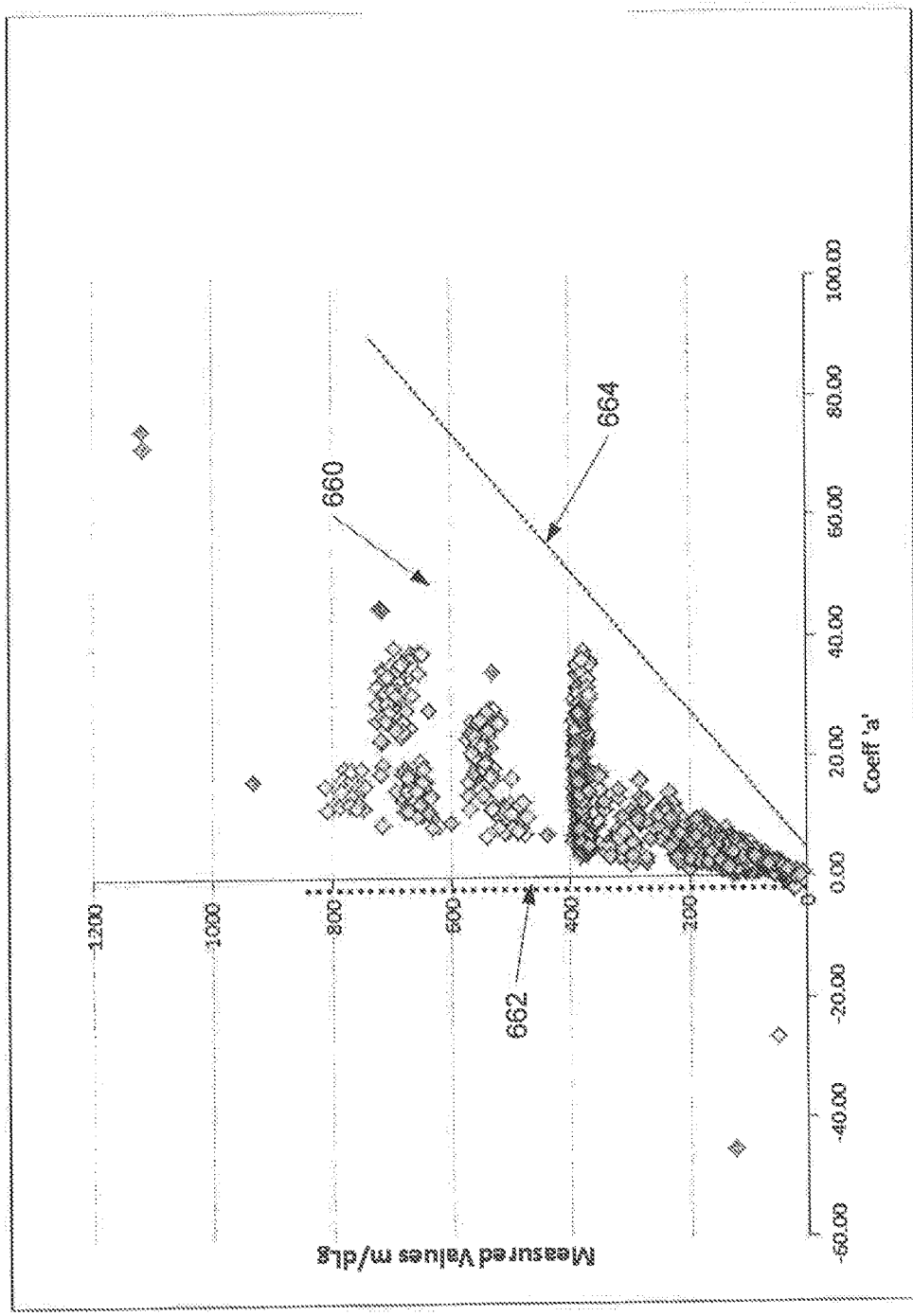

Referring to FIG. 11a, each data point shown in the figure is a mean coefficient for a particular analyte concentration. As an example, for a mean coefficient 608 for a particular analyte concentration, a lower limit point 610 of the range of coefficients 602 is defined as a selected first number of negative standard deviations 612 from the mean coefficient 608. An upper limit point 614 of the range of coefficients 602 is defined as a selected second number of standard deviations 616 from the mean coefficient 608. In some examples, the selected number of standard deviations (or sigmas) can be between four to six. The selected first number and the selected second number of standard deviations (612, 616) can be the same (i.e. have the same magnitude) or can be different (i.e. have different magnitudes) depending on the analyte. For each of the different analyte concentrations, a lower limit point and an upper limit point of the range of coefficients 602 at a subject concentration is determined in a similar fashion.

The lower limit 604 of the range of coefficients 602 is determined by computing a best-fit line through the lower limit points. The upper limit 606 of the range of coefficients 602 is determined by computing a best-fit line through the upper limit points. As can be seen, the lower limit 604 and the upper limit 606 varies with oxygen concentration. For example at an oxygen concentration of 100, the lower limit is −30 and the upper limit is +45. The lower limit of the range of coefficients changes to −85 and the upper limit changes to +10 when the oxygen concentration changes to 500.

Depending on an analyte, a lower limit and/or an upper limit of a range of coefficients may be invariant to changes in analyte concentration (i.e., the limit does not change with analyte concentration). For example, FIG. 11b shows an example range of coefficients for sodium 640 in which a lower limit 642 and an upper limit 644 do not vary with sodium concentration. The lower limit 642 is fixed at −1.75 and the upper limit 644 is fixed at 3 for all concentrations of sodium. FIG. 11c shows an example range of coefficients for glucose 660. A lower limit 662 of the range of coefficients 660 does not vary with glucose concentration and is fixed at −2. An upper limit 664 of the range of coefficients 660 varies with glucose concentration. The upper limit 664 of the range of coefficients 660 increases (approximately) linearly with an increase in glucose construction.

Turing now to the approach for increasing sample throughput in an automated clinical analyzer, the approach includes predicting the end point response time of a sensor for the analysis of an analyte in a sample, such as a body fluid sample, and for improving measurement reliability by detecting outliers and qualifying parameters in curve fitting equations. According to various embodiments described herein, the present invention describes techniques for extrapolating an end point response of a sensor by determining a curve fitting equation derived from data signals generated by the sensor in response to being exposed to a sample. In various embodiments, the curve fitting equation will be a second degree logarithmic polynomial having a general form of $s(t)=a(\log(t))^2+b(\log(t))+c$, where a, b, and c are the polynomial coefficients that are determined based on the converted data points, and s(t) is the calculated sensor output at a particular time t. In this way, a sample analysis system may no longer need to wait the entire duration of the sensor end point response time to analyze a sample and provide a determination of the concentration of the analyte measured by the sensor in the sample. Moreover, by reducing the sensor response time, and therefore, the sample exposure time, the sensor recovery time, which is the time the sensor takes to recover is also reduced, allowing for greater throughput.

In order to further elucidate the present teachings, the following definitions are provided.

"Critical points," as used herein, refers to local extremum points and inflection points.

A "local extremum point," as used herein, refers to a point in a function at which the first derivative exists and is zero.

An "inflection point," as used herein, refers to a point in a function at which the second derivative changes sign.

An "outlier," as used herein, refers to a sample data point that is numerically distant from the rest of the data.

A "residual," as used herein, is the difference between a sample data point and the estimated function value as obtained by a curve fitting equation.

A "Studentized residual," as used herein, is the quantity resulting from the division of a residual by an estimate of its standard deviation.

"DFFITS," as used herein, is an expression that quantifies how influential a point is in a statistical regression. In its classical definition, DFFITS equals the Studentized residual times $\sqrt{h_{ii}/(1-h_{ii})}$, where $h_{ii}$ is the leverage for the point; leverage, $h_{ii}$, is defined as elements $h_{ii}$ of the Hat Matrix, H, which identifies the amount of leverage exerted by the ith observation $y_i$ on the ith fitted value. Another version of an expression that quantifies how influential a point is in a statistical regression is a measure that indicates the change at an extrapolated point caused by removing an individual point from the regression fit; examples of such measure, where 55 is the time corresponding to the extrapolated point are $$\text{Delta55}_i = \frac{[1 \; \log_{10} 55] * A * \begin{bmatrix} 1 \\ \log_{10} t \end{bmatrix} * R_i}{1 - H_{ii}}$$

For a linear fit in log(t) (where A is a matrix related to the Hat Matrix and defined as $$A = (X^T * X)^{-1})$$

and $$\text{Delta55}_i = \frac{[1 \; \log_{10} 55 (\log_{10} 55)^2] * A * \begin{bmatrix} 1 \\ \log_{10} t \\ (\log_{10} t)^2 \end{bmatrix} * R_i}{1 - H_{ii}}$$

For a quadratic fit in log(t). The above expressions are variations of the classical DFITTS or $\text{DFFITS}^2$.

"DFFITS," as used herein, refers to the classical definition or the measure that indicates the change at an extrapolated point caused by removing an individual point from the regression fit.

The "hat matrix, H," as used herein, sometimes also called projection matrix, is a matrix that maps the vector of observed values to the vector of fitted values.

Returning to FIG. 1a, the analyte concentration measurement application 110 may generally be configured to communicate with the sensors 140. The analyte concentration measurement application 110 may include one or more modules configured to perform specific functions or tasks in order to determine the concentration of an analyte within a sample. In various embodiments, the analyte concentration measurement application 110 may include a sensor communication module 112, a data point reporting module 114, a data point selection module 116, a curve fitting module 118, an extrapolation module 120, a validation module 122, an analyte concentration reporting module 124 and a curve fit quality module 126. It should be appreciated that in various embodiments, the analyte concentration measurement application 110 may include additional modules for performing additional tasks, or may include only some of the modules listed above.

The analyte concentration measurement application 110 may generally be configured to receive data signals generated by a sensor upon being exposed to an analyte within a sample, record data points extracted from the data signals, evaluate the data points on a function of time scale, a logarithmic function of time scale in one embodiment, determine a curve that matches the evaluated data points, determine a curve fitting equation that can be utilized to extrapolate an end point response of the sensor, and accurately estimate the concentration of the analyte based on the extrapolated end point response of the sensor.

In various embodiments, the sensor communication module 112 may be configured to receive data signals from the sensors 140. In some embodiments where the sensors may be electrochemical sensors, the data signals may represent an amperometric output that may be measured in Amperes, or a voltmetric output that may be measured in Volts. In various embodiments, these data signals may vary over time, and typically may generate an output value that eventually stabilizes over time. The stabilized output value may typically be the end point response of the sensor. It should be appreciated that any type of sensor that can generate a data output signal in response to being exposed to an analyte may be utilized as a sensor 140.

The data point recording module 114 may be configured to capture and record data points from the generated data signals. The data points may be stored in the memory of the automated clinical analyzer 102, or at any other storage medium accessible by the analyte concentration measurement application 110. In various embodiments, the data point recording module 114 may record a measurement of the data signal after every nth fixed period of time. The fixed period of time may be predefined by the analyte concentration measurement application 110. It should be appreciated that the fixed period of time may be defined by the technological limitations of existing systems and is not intended to be limited to any particular range. However, in some embodiments, the fixed period of time may range from a millisecond to a few seconds. In alternate embodiments, the data point recording module 114 may record a measurement of the data signal after random or variable periods of time.

The data point selection module 116 may be configured to select pertinent data points from the recorded data points. In various embodiments, the data point selection module 116 may select data points that when plotted on a function of time scale, a logarithmic function of time scale in one embodiment, may allow the analyte concentration measurement application to determine a curve that closely fits the selected data points and also results in predicting an end point response of the sensor that is within acceptable limits. In various embodiments, data points that may provide the most accurate results may be selected from a time range that is empirically determined, and may vary depending on characteristics of the sensor and the analyte.

In various embodiments, the data point selection module 116 may select a series of data points corresponding to a kinetic region time range from the recorded data points. The kinetic region time range refers to any time range in which the data points are within the kinetic region of a sensor response. Typically, the kinetic region occurs from a first time when the sensor is exposed to the analyte, to a second time when the data signals generated by the sensor are not substantially similar to the end point response of the sensor i.e. before the sensor response reaches equilibrium. In other words, once the data signals generated by the sensor become substantially similar to the end point response of the sensor, the data signals are being generated in an equilibrium region. In various embodiments, the data point selection module 116 may select a series of data points corresponding to a portion of a kinetic region time range. In one embodiment, the time range may begin at about fifteen seconds after the sensor is exposed to the analyte. Moreover, the time range may end at about thirty seconds after the sensor is exposed to the analyte. Additional details regarding which data points to select are provided below with respect to FIG. 4.

The curve fitting module 118 may be configured, in one embodiment, to convert the selected data points to a function of time scale, a logarithmic function of time scale in one embodiment, such that the converted data points can be evaluated on a function of time scale. The curve fitting module may then determine a curve that closely matches the evaluated data points. The curve fitting module may use conventional curve fitting methods such as regression analysis or least square methods.

In various embodiments, the equation describing the curve (also referred to as the curve fitting equation) is a polynomial in a function of time, in one embodiment, a logarithm of time (log (t)), and a predetermined value of the function of time (in one embodiment, a logarithm of time) at which a critical point occurs is provided, the predetermined value providing a relationship between polynomial coefficients.

In various embodiments, the curve fitting module 118 may plot the selected data points on a logarithmic function of time scale, and determine a curve that closely matches or fits the plotted data points.

Upon determining the curve, the curve fitting module may determine a curve fitting equation corresponding to the curve. In various embodiments, the curve fitting equation is of the form $s(t)=a*(\log(t))^2+b*\log(t)+c$, wherein t represents time and a, b and c are fit parameters for a second order polynomial, the critical point is an extremum point, and the predetermined value (V) provides a relationship between the fit parameters b and a of the form $b=-2aV$; the fit parameters a and c being determined based on the initial sensor response. The precise values of a, b, and c, which are determined empirically for each sensor configuration used, depend in part upon the concentration of the analyte, the size of the sample, the temperature, the geometry of the sensor apparatus setup, and other parameters.

In one instance, the invention not been limited to that instance, the predetermined value of the time at which time at which a critical point occurs is selected to be the time at which the end point is desired. In other instances, not a limitation of the invention, times beyond the endpoint time can be selected as the predetermined time.

The extrapolation module 120 may be configured to extrapolate an end point response of the sensor by solving the curve fitting equation for a time within the equilibrium region of the curve. In various embodiments, the analyte concentration measurement application 102 may utilize empirical methods to determine a time that is within the equilibrium region of the curve, and then store the determined equilibrium region time as a predefined time with which to solve the curve fitting equation.

The validation module 122 may be configured to validate the calculated end point response by determining the coefficient of variation (CV) and the coefficient of determination ($R^2$). The following formulas for determining the coefficient of variation (CV) and the coefficient of determination ($R^2$) are well known in the art and may be used by the validation module 122 to validate the calculated end point response.

$$CV = \text{standard deviation}(y_i)/\text{mean}(y_i); \text{ and}$$

$$R^2 = 1 - (\text{sum}((y_i - f_i)^2)/(\text{sum}((y_i - \text{mean}(y_i))^2));$$

where $y_i$ and $f_i$ are the observed and calculated values at a specified time, respectively.

The curve fit quality module 126 may be configured to determine and improve usefulness of the curve fitting equation corresponding to the analyte. In one or more embodiments, the curve fit quality module 126 may be configured to, after the curve fitting equation has been obtained, to perform the analysis described herein below. The curve fit quality module 126 may be configured to determine an outlier candidate with a largest residual. Conventional methods for determining an outlier candidate with a largest residual, such as the Studentized residual or Dixon methods, can be used. Once the outlier candidate with largest residual is selected, the residual of the outlier candidate is compared to a residual limit. The residual limit can be predetermined from past experience, analytical considerations or other approaches. If the residual of the outlier candidate exceeds the residual limit, the outlier candidate is classified as an outlier. If the residual of the outlier candidate, which had the largest residual, is less than or equal to the residual limit, the curve fit quality module 126 can pass operation to another module since other residual candidates with similar residuals will also be within the residual limit. If the outlier candidate has been classified as an outlier, the curve fit quality module 126 is configured to obtain a measure of the effect of the outlier on the parameters of the curve fitting equation. Conventional methods for obtaining a measure of the effect of the outlier such as, but not limited to, Cook distance, DFFITS and DFBETAS, may be used. The measure of the effect of the outlier is compared to a predetermined measure limit. The measure limit can be predetermined from past experience, analytical considerations or other approaches. If the measure of the effect of the outlier exceeds the predetermined measurement limit, an outlier count, initially set to zero, is incremented, the outlier count is compared to a predetermined outlier limit, and the outlier is removed from the data points. A modified set of data points is obtained by removing the outlier or the outlier candidate from the data points and the above analysis is performed again.

It should be appreciated that by way of the present disclosure, the sample exposure time is reduced as the sensor response time is reduced. As a result of the reduced sample exposure time, the sensors, and in particular, enzymatic sensors, including but not limited to sensors for measuring glucose and lactate, may have shortened sensor recovery times. As the sensors can recover faster, a greater throughput can be achieved.

Exemplification

The following exemplary embodiments are presented to further elucidate the invention but it should be noted that the invention is not limited only to the exemplary embodiments.

The analyte concentration recording module 124 determines the concentration of the analyte within the sample using the calculated end point response and report the analyte concentration with a flag if the validation module 122 determines that the CV and $R^2$ are not within acceptable limits. Conversely, if the CV and $R^2$ are within acceptable limits, then the analyte concentration recording module 124 may report the concentration of the analyte without a flag. Analytes that may be measured according to the method of the invention include, but are not limited to for example, hematocrit, the ion concentration of calcium, potassium, chloride, sodium, glucose, lactate, creatinine, creatine, urea, partial pressure of O2 and/or CO2, or any other analyte for which a sensor exists. In various embodiments, the flag may be a data bit that may be represented visually as a flag, a symbol, or aurally, as a beep, a tone, or in any other manifestation that may indicate to a user that the either the CV or the $R^2$ is not within acceptable limits.

Figure 2:
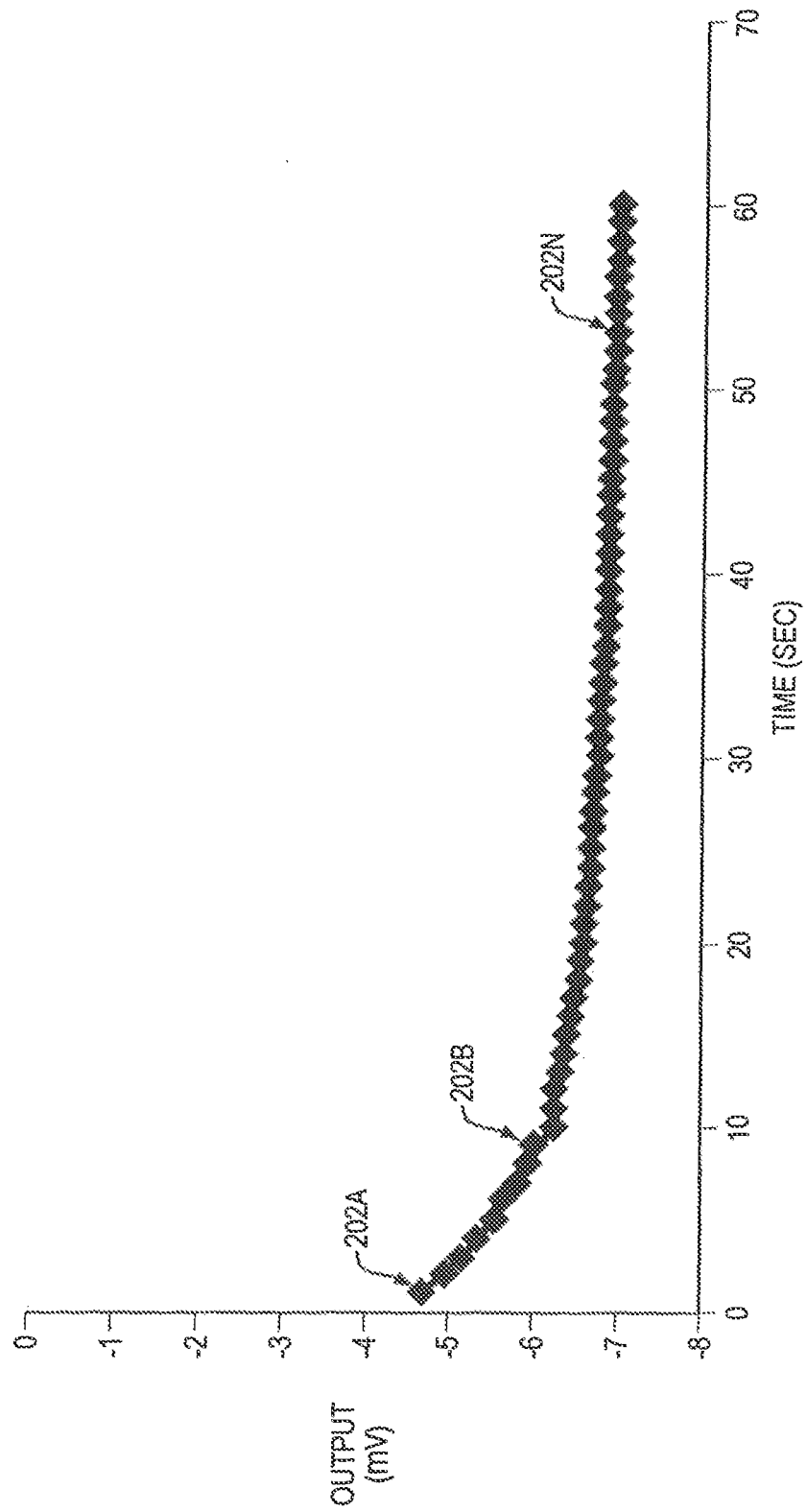
FIG. 2 shows an exemplary plot of voltage versus time for experimental data generated by a sensor for measuring the concentration of glucose according to one embodiment of the invention.

Referring now to FIG. 2, an exemplary plot of voltage versus time for experimental data generated by a sensor for measuring the concentration of glucose is shown. In particular, the plot shows a series of data points 202A-N that are captured from a data signal generated by the sensor 140. The data points indicate an output value, such as a voltage, current, or charge. In various embodiments, data points from the generated signal may be recorded over time and plotted against time. The plot shown in FIG. 2 is generated by plotting the recorded data points 202A-N against time. In the present embodiment, the data points are recorded every second. However, in various embodiments, data points may be recorded at time intervals that are less than or more than a second.

It should be appreciated that by recording data points at time intervals less than a second, more data is generated, which may allow for a more accurate plot, but may also utilize additional computing resources, which may be undesirable, depending on system resources. Alternatively, data points that are recorded at time intervals substantially exceeding a second may provide a less accurate plot. In any event, the length of the time intervals between data points is an implementation choice that may be determined based on various factors, such as the end point response time of the sensor, limitations with respect to computing resources, the nature of the sensor and analyte, and the like.

Figure 3:
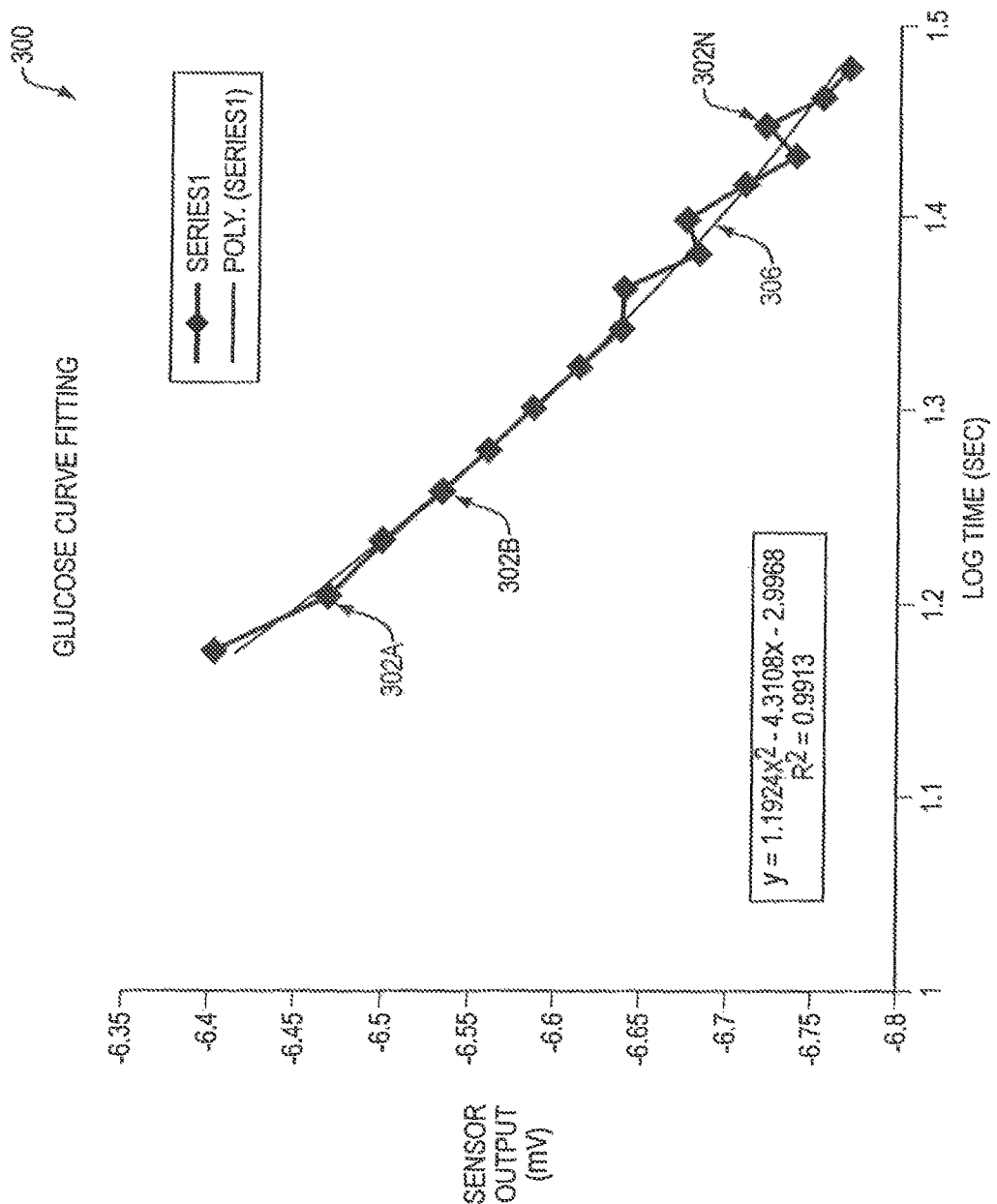
FIG. 3 shows an exemplary plot of voltage versus logarithmic function of time using a portion of the experimental data of FIG. 2 according to one embodiment of the invention.

Referring now to FIG. 3, an exemplary plot of voltage versus a logarithmic function of time using a portion of the experimental glucose data of FIG. 2 is shown. As described above, once the data points corresponding to the data signals received from the sensor are recorded, the data point selection module 116 may select pertinent data points from the recorded data points. The selected data points may then be converted to a logarithmic scale, such as base 10 or natural log. Upon converting the data points to the logarithmic scale, the converted data points 302A-N are plotted as voltage values versus logarithmic function of time.

As shown in FIG. 3, once the converted data points 302A-N are plotted on the voltage versus logarithmic function of time scale, the plot 300 may be shown. This allows the curve fitting module 118 to determine a curve 306 that closely matches the converted data points 302A-N. Then, the curve fitting module 118 may determine a curve fitting equation based on the curve 306 that is simpler than existing curve fitting equations utilized in sensor technologies. Existing curve fitting equations require finding roots of non-linear equations, whereas the techniques disclosed herein do not require finding such roots. Finding roots of non-linear equations is computationally intensive, and when dealing with systems that have high throughputs, the severity of the problem becomes even more apparent. As a result, by utilizing curve fitting equations that do not require finding roots of non-linear equations, the automated clinical analyzer 10 requires fewer computational resources than existing systems. This translates to various advantages over existing systems, including but not limited to increased throughputs, reduced costs of manufacture, and a smaller physical and energy footprint. Further, it should be appreciated that the display step may not be necessary as the curve fitting equation may be determined without having to plot data points or draw a curve that fits the data points.

According to various embodiments, the curve fitting equation may typically be a second degree logarithmic equation that has a general form of $$s(t)=a(\log(t))^2+b(\log(t))+c,$$

where a, b, and c are the polynomial coefficients that are determined based on the converted data points, and s(t) is the calculated sensor output at a particular time t. In one embodiment, a predetermined value of the logarithm of time at which a critical point occurs is provided, the predetermined value providing a relationship between polynomial coefficients. The precise values of a, b, and c. which are determined experimentally or analytically (for example, using regression analysis) for each sensor configuration used, depend in part upon the concentration of the analyte, the size of the sample, the temperature, the geometry of the sensor transducer setup, and other parameters. In one instance, the critical point is an extremum point, and the predetermined value (V) provides a relationship between the fit parameters b and a of the form b=−2aV; the fit parameters a and c being determined based on the sensor response by curve fitting techniques (such as, but not limited to, regression analysis and least square methods). Once the values of a, b, and c have been determined for a sensor configuration, the curve fitting equation may be used to rapidly estimate the concentration of the analyte in the sample. According to the invention, there is no need to wait for the sensor to provide its final reading to determine the analyte concentration.

It should be appreciated that the selection of the data points to be converted plays an important role in determining the accuracy of the curve fitting equation. Although conventional wisdom would suggest that the greater the number of data points utilized for determining the curve fit, the better.

The present invention discloses that such wisdom is not necessarily true. Rather, the range from which the data points are selected may play an even more important role. In various embodiments, the data points selected to be converted to the logarithmic function of time scale were the data points generated from 15-30 seconds after the analyte was first exposed to the sensor. In other embodiments, data points from 15-35 seconds after the analyte was first exposed to the sensor were used without significant improvements in accuracy. Similarly, data points from 10-25 seconds after the analyte was first exposed to the sensor were used but produced some results that were not accurate enough. It should be appreciated that the data points selected may vary based on the type of sensor and analyte, end point response time, amongst other factors. In various embodiments, the time range for selecting the data points may be determined through empirical methods.

As described above, the end point response value of the sensor may be calculated by solving the equation for a time that is within the equilibrium region of the sensor response curve. Once the end point analyte related value is calculated using the curve fitting equation, the end point response value is converted to a value corresponding to the concentration of the analyte, using, for example, a method comprising a calibration value (e.g. a ration, a calibration point, a difference value, etc.).

Figure 4:
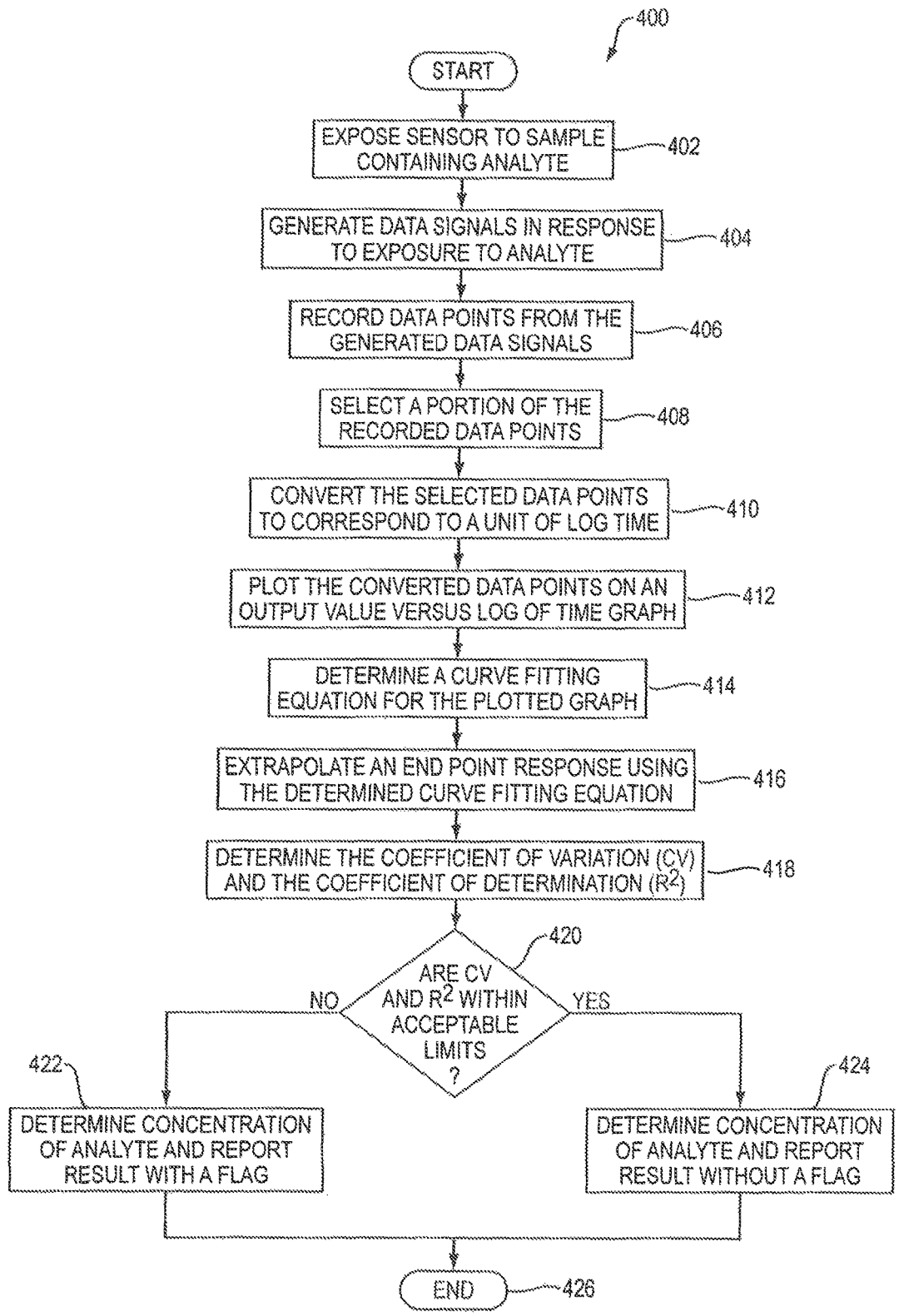
FIG. 4 is an exemplary logical flow diagram for predicting the end point response of the sensor according to one embodiment of the invention.

Referring now to FIG. 4, an exemplary logical flow diagram for estimating the concentration of an analyte within a sample is shown. A routine 400 begins at operation 402, where the sensor 140 is exposed to a sample containing the analyte. As described above, the electrochemical sensor 140 may be responsive to the levels of concentration of an analyte within the sample.

From operation 402, the routine 400 proceeds to operation 404, where the sensor 140 may generate one or more data signals in response to the exposure to the analyte. In various embodiments, the data signals may be in the form of a voltage, current, charge, or any other type of measurable output. These data signals are continuously being generated by the sensor 140 while being exposed to the analyte.

From operation 404, the routine 400 proceeds to operation 406, where the data point recording module 114 may record data points from the data signals. The granularity at which these data points are recorded may be determined by the type of sensor, the amount of analyte, the size of the sample, the temperature, amongst other factors. In one embodiment, the data signals are recorded every second. However, it should be appreciated that the frequency at which these data points are recorded may be greater than or less than one data point per second. The data points may be stored within the memory of the automated clinical analyzer 102, or may be stored remotely at a location that is accessible by the analyte concentration measurement application 110.

From operation 406, the routine 400 proceeds to operation 408, where the data point selection module 116 may select a portion of the data points recorded by the data point recording module 114. In various embodiments, the data point selection module 116 may select data points that, when plotted, may help determine a curve that has an equation, which, when extrapolated to a time in the future, generates a result that is proximate to the actual result of the sensor 140. In various embodiments, the data point selection module 116 may select any number of data points. There is a countervailing balance that the data point selection module 116 has to consider when selecting data points. Selecting too many data points may also increase the number of outliers, which may adversely affect the accuracy of the curve being fitted, as well as selecting data points that are too far ahead in time may delay the time in which the automated clinical analyzer 102 may determine the analyte concentration. In particular, selecting the first few data points that are recorded may cause the automated clinical analyzer 102 to produce inaccurate results. This is because the sensors 140, when initially exposed to the analyte, may generate noise signals, amongst other undesirable affects. Accordingly, based on empirical methods, data points selected from the kinetic region but after the initial response of the sensor 140 may generate the most accurate results, while balancing the need to determine the concentration of analyte in the shortest time, without significantly compromising on accuracy.

From operation 408, the routine 400 proceeds to operation 410, where the curve fitting module 118 converts the selected data points having an output value corresponding to a particular time to a unit of logarithmic function of time. In various embodiments, the base of the logarithmic scale may be base 10, or natural log (ln e). By doing so, a curve generated by the plotted converted data points may be more accurate and utilizes less data points than existing curve fitting equations.

From operation 410, the routine 400 proceeds to operation 412, where the curve fitting module 118 may plot the converted data points on a graph. In various embodiments, the Y-axis is an output value gathered from the data signal generated by the sensor 140, and the X-axis is a logarithmic function of time. From operation 412, the routine 400 proceeds to operation 414, where the curve fitting module 118 may determine a curve fitting equation for the plotted graph. In various embodiments, the curve fitting module 118 may determine a curve fitting equation that is a second degree logarithmic polynomial having the form $s(t)=a(\log(t))^2+b(\log(t))+c$, where a, b, and c are the polynomial coefficients that are determined based on the converted data points, and $s(t)$ is the calculated sensor output at a particular time t. The precise values of a, b, and c. which are determined experimentally or analytically for each sensor configuration used, depend in part upon the concentration of the analyte, the size of the sample, the temperature, the geometry of the setup, and other parameters. It should be appreciated that the curve fitting module may not necessarily plot the data points to determine a curve that fits the data points. In some embodiments, the curve fitting module 118 may be able to determine a curve that fits the data points without having to plot the data points. Commercially available curve fitting software may be utilized to determine a curve and a corresponding equation that fits the selected data points.

From operation 414, the routine 400 proceeds to operation 416, where the extrapolation module 120 extrapolates the calculated end point response of the sensor 140 by solving the curve fitting equation for a time that falls within the equilibrium region. From operation 416, the routine 400 proceeds to operation 418, where the validation module 122 validates the end point response for accuracy. According to some embodiments, the validation process includes determining the coefficient of variation (CV) and the coefficient of determination ($R^2$) using the formulas of CV and $R^2$ that are presented above.

From operation 418, the routine 400 proceeds to operation 420, where the validation module 122 determines whether the CV and the $R^2$ are within acceptable limits predefined by the automated clinical analyzer 102. In various embodiments, these limits may allow for the CV and $R^2$ to fall within an acceptable range, which may be known by those persons having ordinary skill in the art. In one embodiment, the limits may allow for the $R^2$ to fall between 0.98 and 1. The coefficient of determination ($R^2$) indicates how well the data and the curve fit function match. The closer the value of $R^2$, the better the match.

If, at operation 420, the validation module 122 determines that either the CV, $R^2$, or both the CV and $R^2$ not within the acceptable limit, the routine 400 proceeds to operation 422, where the analyte concentration reporting module 124 determines the concentration of the analyte using the extrapolated end point response, and reports the analyte concentration with a flag indicating that the result does not fall within the acceptable limits.

However, if at operation 420, the validation module 122 determines that both the CV and $R^2$ are within the acceptable limit, the routine 400 proceeds to operation 424, where the analyte concentration reporting module 124 determines the concentration of the analyte using the extrapolated end point response, and reports the analyte concentration without a flag. From operation 422 and 424, the routine 400 ends at operation 426.

According to various embodiments, it may be desirable to provide a system for calibration of the sensors 140. A self-calibration system for measuring the analyte concentration may be used to correct for imprecision in the manufacturing of the sensor, thus reducing the time and cost of manufacture. In addition, the self-calibration system may be used to compensate for small magnitudes of noise generated by the sensor or other components of the automated clinical analyzer 102.

Figure 5A:
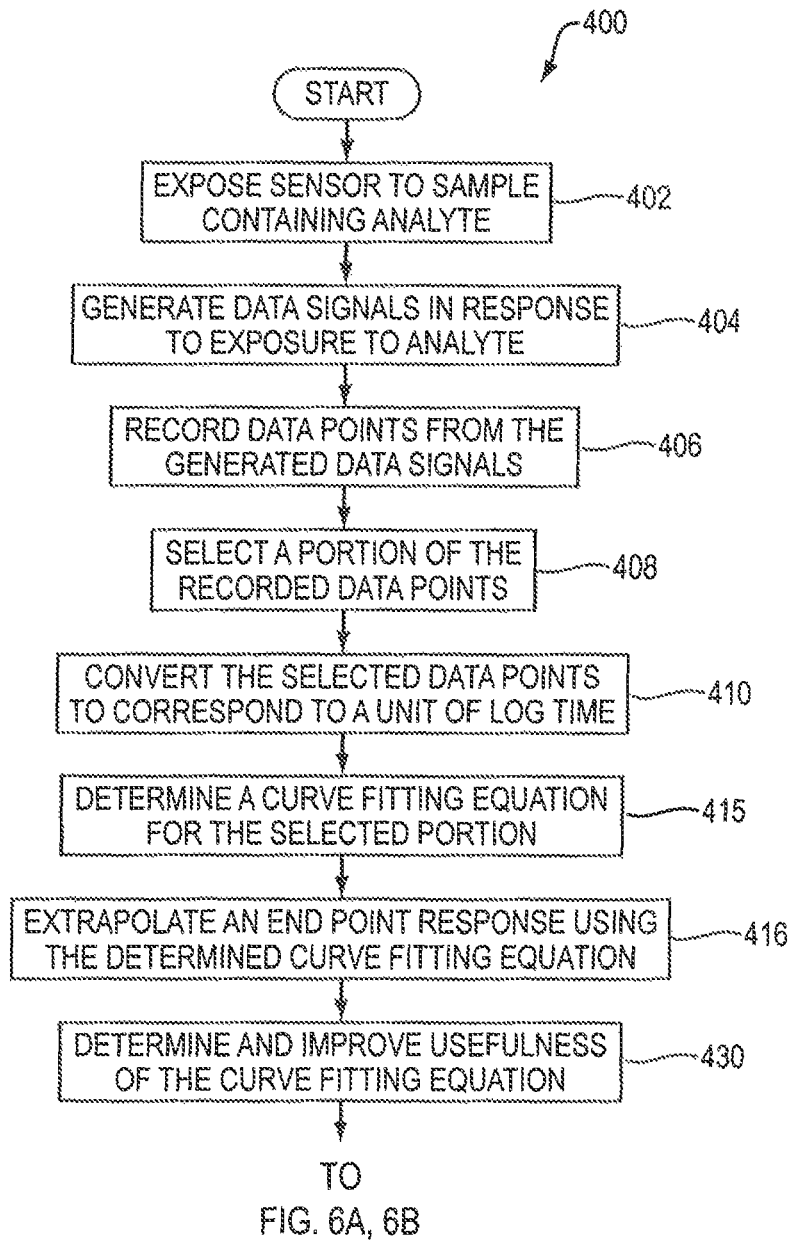
FIGS. 5a and 5b are exemplary logical flow diagram for analysis of samples according to embodiments of the invention.

Referring to FIG. 5a, an exemplary flow diagram for determining and improving the usefulness of the curve fitting equation is shown therein. Another examples of routine 400 begins at operation 402, where the sensor 140 is exposed to a sample containing the analyte. As described above, the electrochemical sensor 140 may be responsive to the levels of concentration of an analyte within the sample.

From operation 402, the routine 400 proceeds to operation 404, where the sensor 140 may generate one or more data signals in response to the exposure to the analyte. In various embodiments, the data signals may be in the form of a voltage, current, charge, or any other type of measurable output. These data signals are continuously being generated by the sensor 140 while being exposed to the analyte. The routine 400 then proceeds through operations 406 to 410, as described herein above.

From operation 410, the routine 400 proceeds to operation 415 in which a curve fitting equation is determined for the selected data points. The curve fitting equation may be determined by conventional methods such as, but not limited to, regression analysis or the least square methods. According to various embodiments, the curve fitting equation may typically be a second degree logarithmic equation that has a general form of $$s(t)=a(\log(t))^2+b(\log(t))+c,$$

where a, b, and c are the polynomial coefficients that are determined based on the converted data points, and s(t) is the calculated sensor output at a particular time t. In one embodiment, a predetermined value of the logarithm of time at which a critical point occurs is provided, the predetermined value providing a relationship between polynomial coefficients. The precise values of a, b, and c. which are determined experimentally or analytically (for example, using regression analysis) for each sensor configuration used, depend in part upon the concentration of the analyte, the size of the sample, the temperature, the geometry of the sensor transducer setup, and other parameters. In one instance, the critical point is an local extremum point, and the predetermined value (V) provides a relationship between the fit parameters b and a of the form b=−2aV, the fit parameters a and c being determined based on the sensor response.

From operation 415, the routine 400 proceeds to operation 416, where the extrapolation module 120 extrapolates the calculated end point response of the sensor 140 by solving the curve fitting equation for a time that falls within the equilibrium region. From operation 416, the routine 400 proceeds to operation 430 in which the curve fit quality module 126 determines and improves the usefulness of the curve fitting equation. Embodiments of the logic flow diagram for operation 430 are shown in FIGS. 6a, 6b, 7a, 7c.

Figure 5B:
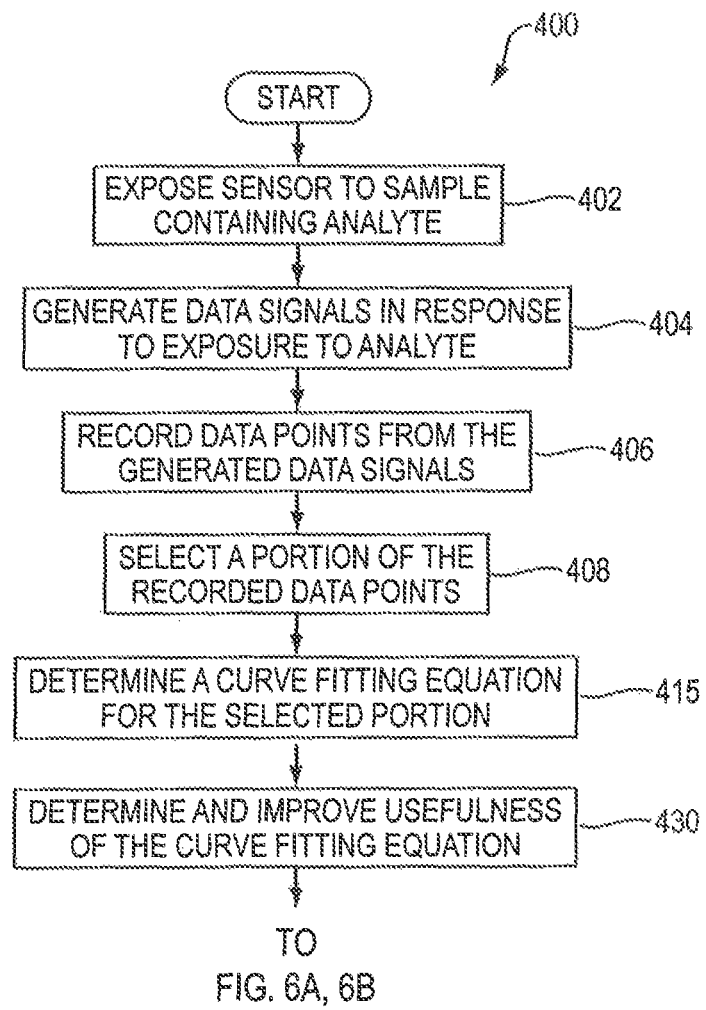

Another embodiment of the logic flow diagram for analyzing data for an analyte is presented in FIG. 5b. As stated above, embodiments in which only some of the modules in the automated clinical analyzer 102 shown in FIG. 1 are used are within the scope of this invention. There are numerous automated clinical analyzers in which a curve describing a fit for the data points can be used even if the curve fitting equation is not used for extrapolation. In the embodiment shown in FIG. 5b, operation 416 is omitted to emphasize that embodiments in which extrapolation is not present are also within the scope of these teachings.

Figure 6A:
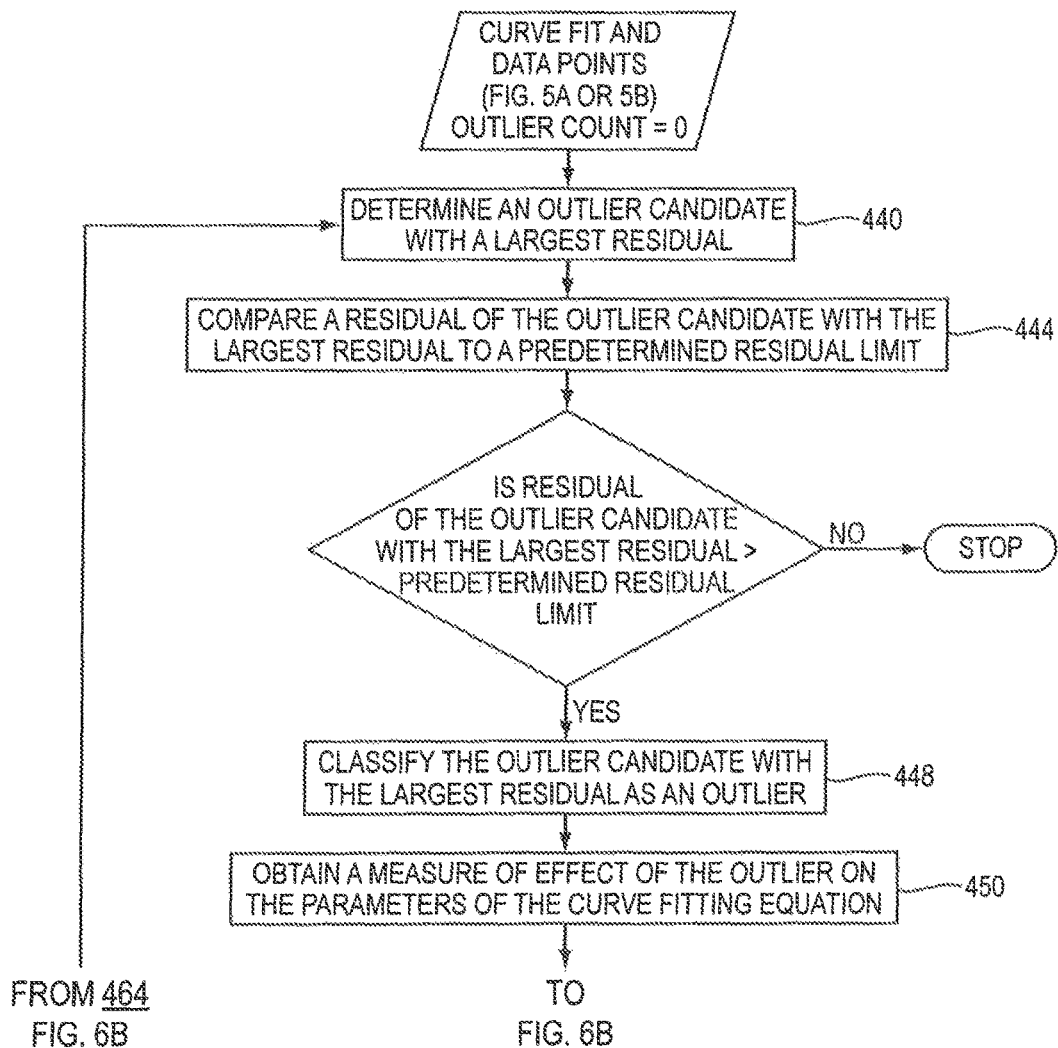
FIGS. 6a and 6b are exemplary logical flow diagram for determining and improving usefulness of the curve fitting equation according to embodiments of the invention.
Figure 6B:
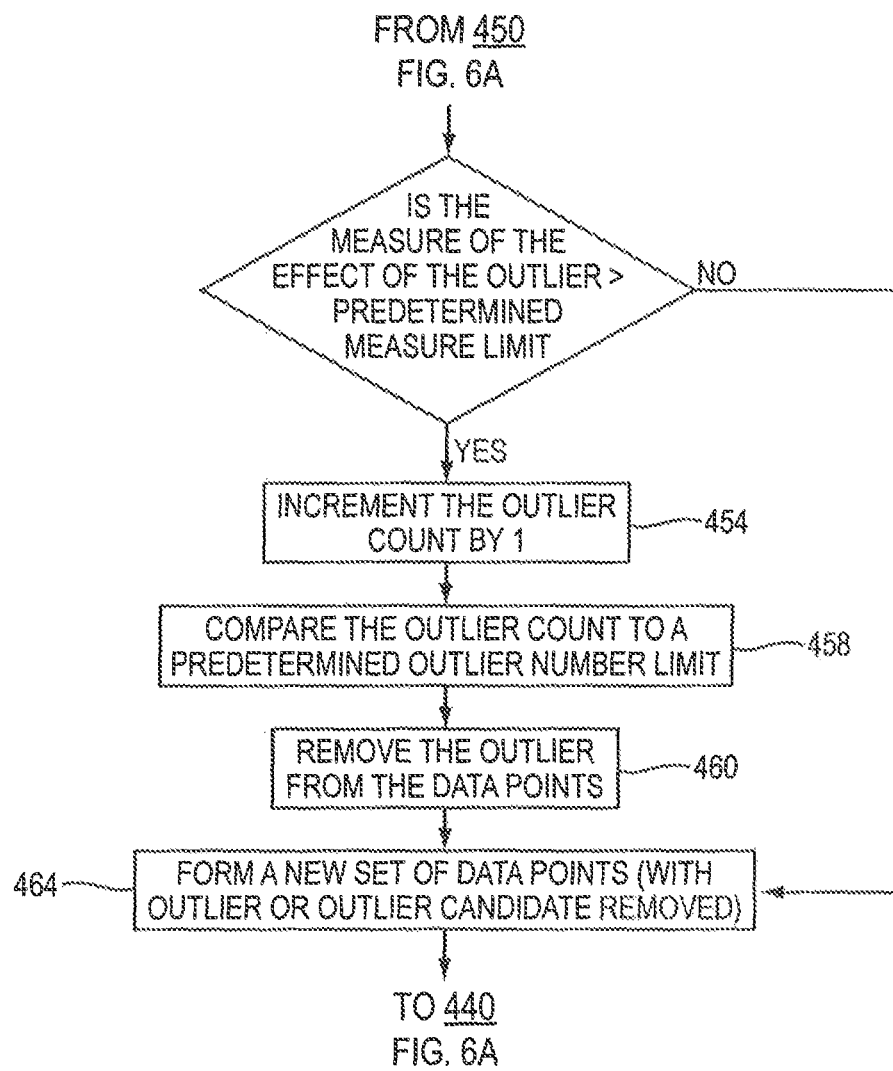

One embodiment of the logic flow diagram for determining and improving the usefulness of the curve fitting equation is shown in FIGS. 6a and 6b. Referring to FIG. 6a, the logic flow diagram shown therein starts from the curve fit and data points obtained from the flow diagram shown in FIGS. 5a or 5b or equivalently obtained from the data point recording module 114, data point selection module 116 and curve fitting module 118 in FIG. 1. The outlier count is initially set to zero. An outlier candidate with the largest residual is determined (operation 440). The logic flow diagram then proceeds to comparing the residual of the outlier candidate with a predetermined residual limit (operation 444). The residual of the outlier candidate is then compared to a predetermined residual limit. If the residual of the outlier candidate with the largest residual is less than or equal to the predetermined residual limit, the operation stops since any other outlier candidate will have a smaller residual and would be within the predetermined residual limit. If the residual of the outlier candidate is greater than the predetermined residual limit, the outlier candidate with the largest residual is classified as an outlier (operation 448). The logic flow diagram then proceeds to obtain a measure of the effect of the outlier on the parameters of the curve fitting equation (operation 450). The logic flow diagram is continued in FIG. 6b. Referring to FIG. 6b, the measure of the effect of the outlier on the parameters of the curve fitting equation, obtained in operation 450, is compared to the predetermined measure limit. If the comparison of the measure of the effect of the outlier on the parameters of the curve fitting equation with the predetermined measure limit indicates that the outlier has a significant effect on the parameters of the curve fitting equation, the outlier count is incremented by one (operation 454), the outlier count is compared to a predetermined outlier numbers limit (operation 458) and the outlier is removed from the data points (operation 460). If the outlier count is greater than the outlier number, the data set is identified for review. The logic flow diagram then forms a new set of data points with the outlier removed (operation 464). In one instance, a new set of curve fit parameters for the curve fitting equation are obtained using the new set of data points in the curve fitting module 118. The logic flow diagram then returns to determining a new outlier candidate with largest residual for the new data set of data points (operation 440, FIG. 6a). If the comparison of the measure of the effect of the outlier on the parameters of the curve fitting equation with the predetermined measure limit indicates that the outlier does not have a significant effect on the parameters of the curve fitting equation, the logic flow diagram proceeds to forming a new data set of points with the outlier candidate removed (operation 464). In one instance, a new set of curve fit parameters for the curve fitting equation are obtained using the new set of data points in the curve fitting module 118. The logic flow diagram then returns to determining a new outlier candidate with largest residual for the new data set of data points (operation 440, FIG. 6a). Another examples of the routine 400 proceeds until all outliers have been identified although it could be stopped if the outlier count exceeds the predetermined outlier number limit.

Figure 7A:
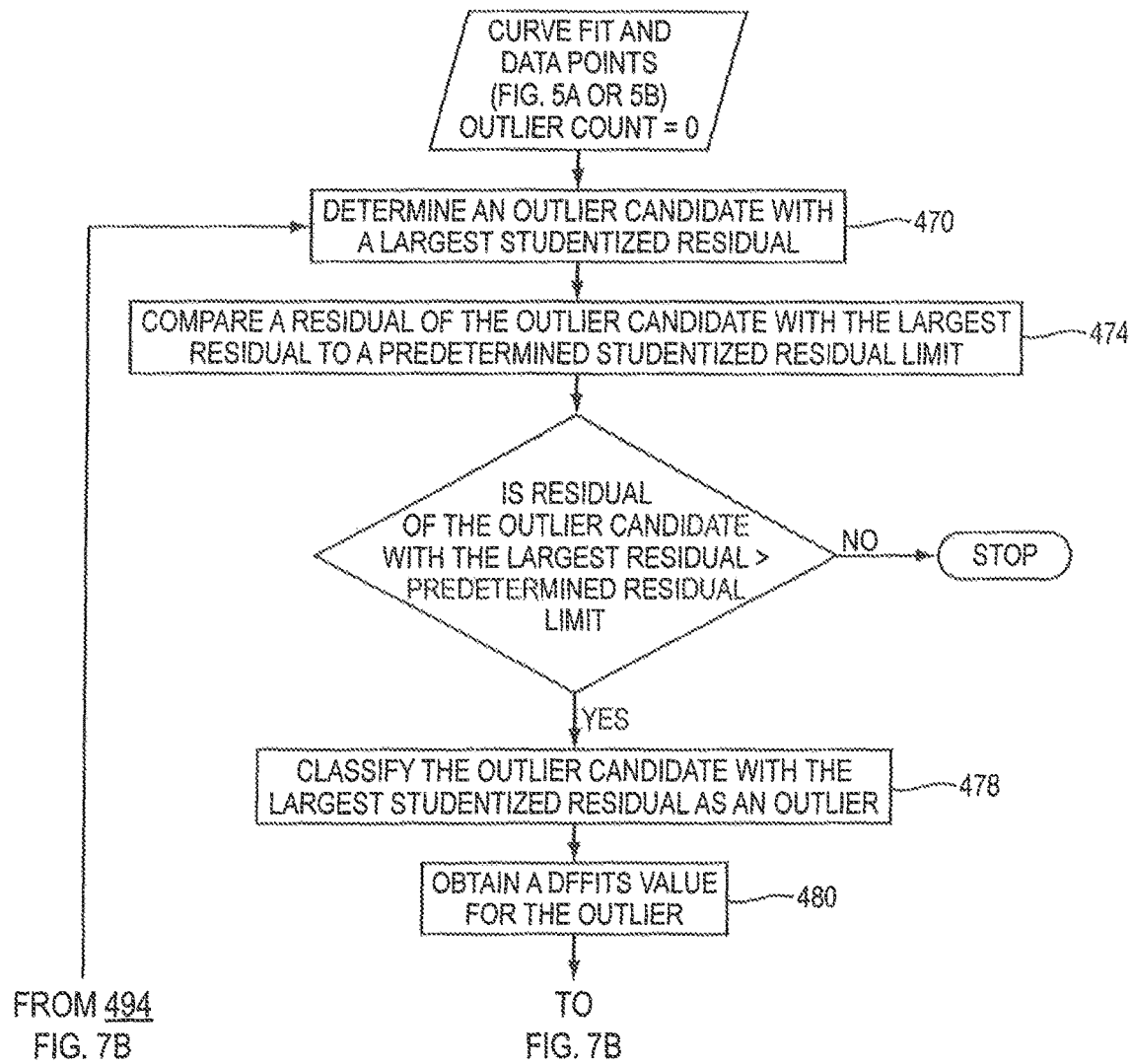
FIGS. 7a and 7b are other exemplary logical flow diagram for determining and improving usefulness of the curve fitting equation according to exemplary embodiments of the invention.
Figure 7B:
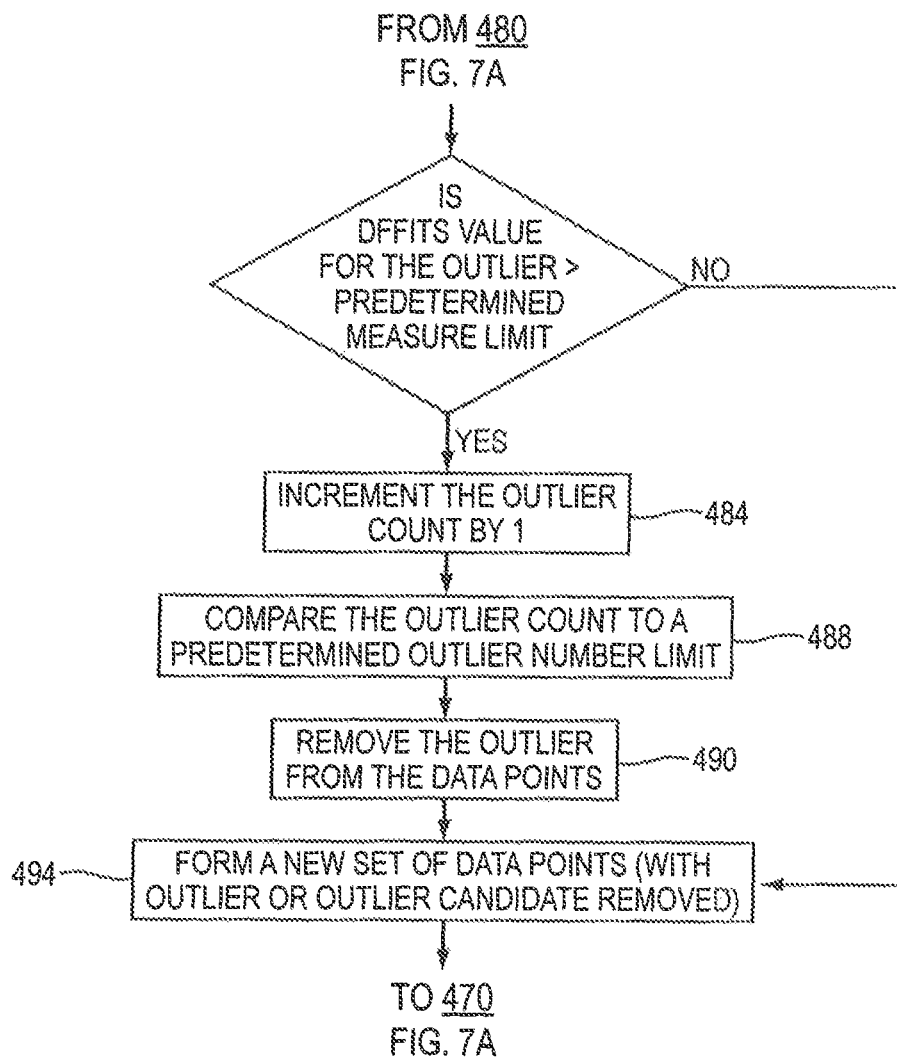

An exemplary embodiment of the logic flow diagram for determining and improving the usefulness of the curve fitting equation is shown in FIGS. 7a and 7b. Referring to FIG. 7a, the logic flow diagram shown therein starts from the curve fit and data points obtained from the flow diagram shown in FIG. 5a or 5b or equivalently obtained from the data point recording module 114, data point selection module 116 and curve fitting module 118 in FIG. 1. The outlier count is initially set to zero. The outlier count is initially set to zero. An outlier candidate with the largest Studentized residual is determined (operation 470). The logic flow diagram then proceeds to comparing the Studentized residual of the outlier candidate with a predetermined Studentized residual limit (operation 474). If the Studentized residual of the outlier candidate with the largest Studentized residual is less than or equal to the predetermined Studentized residual limit, the operation stops since any other outlier candidate will have a smaller Studentized residual and would be within the predetermined residual limit. If the Studentized residual of the outlier candidate is greater than the predetermined Studentized residual limit, the outlier candidate with the largest Studentized residual is classified as an outlier (operation 478). The logic flow diagram then proceeds to obtain a DFFITS value for the outlier (operation 480). The logic flow diagram is continued in FIG. 6b. Referring to FIG. 7b, the DFFITS value for the outlier, obtained in operation 480, is compared to the predetermined DFFITS limit. If the comparison of the DFFITS value for the outlier with the predetermined DFFITS limit indicates that the outlier has a significant effect on the parameters of the curve fitting equation, the outlier count is incremented by one (operation 484), the outlier count is compared to a predetermined outlier numbers limit (operation 488) and the outlier is removed from the data points (operation 490). If the outlier count is greater than the outlier number, the data set is identified for review. The logic flow diagram then forms a new data set of points with the outlier removed (operation 494). In one instance, a new set of curve fit parameters for the curve fitting equation are obtained using the new set of data points in the curve fitting module 118. The logic flow diagram then returns to determining a new outlier candidate with largest Studentized residual for the new data set of data points (operation 470, FIG. 7a). If the comparison of the DFFITS value for the outlier with the predetermined DFFITS limit indicates that the outlier does not have a significant effect on the parameters of the curve fitting equation, the logic flow diagram proceeds to forming a new data set of points with the outlier candidate removed (operation 494). In one instance, a new set of curve fit parameters for the curve fitting equation are obtained using the new set of data points in the curve fitting module 118. The logic flow diagram then returns to determining a new outlier candidate with largest residual for the new data set of data points (operation 470, FIG. 7a). Another examples of the routine 400 proceeds until all outliers have been identified although the routine 400 could be stopped if the outlier count exceeds the predetermined outlier number limit.

Figure 8A:
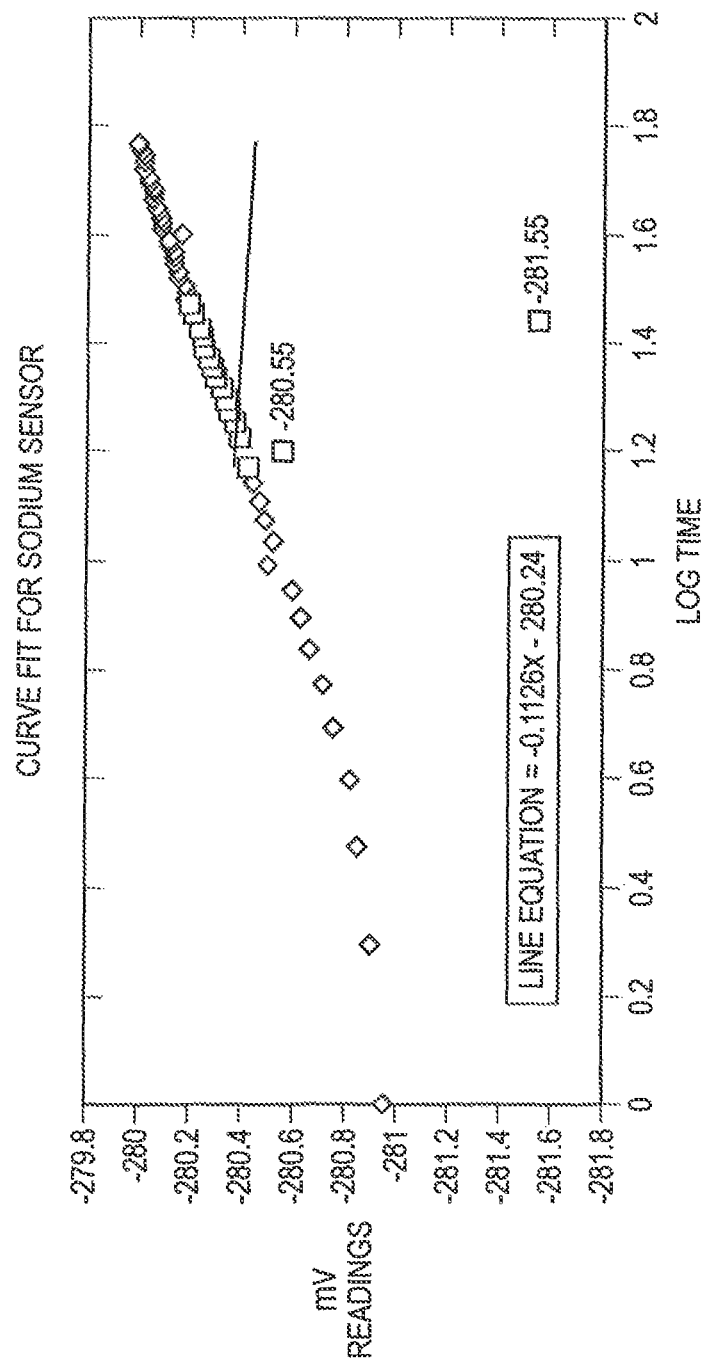
FIGS. 8a, 8b and 8c show an exemplary graphical representations of voltage versus time for experimental data generated by a sensor for measuring the concentration of sodium according to one embodiment of the invention.

An exemplary graphical representation of voltage versus time for experimental data generated by a sensor measuring sodium concentration is shown in FIG. 8a. The exemplary graphical representation shows a series of data points capture from a data signal generated by a sodium sensor 140. The data points shown therein indicate an output value which for the exemplary graphical representation is shown in mVolts. A curve fitting equation, of the type $ax^2+bx+c$ with a=0, is obtained from a curve fitting module 118. For the exemplary graphical representation shown there in the curve fitting equation is $-0.1126x-280.24$. In the exemplary embodiment disclosed herein below determining an outlier candidate with the largest residual is performed by determining a data point with a largest Studentized residual and obtaining a measure of the effect of the outlier is performed by obtaining a DFFITS value (DFFITS, in this exemplary embodiment, refers to the measure that indicates the change at an extrapolated point caused by removing an individual point from the regression fit.) The absolute value Studentized residual limit is 5; Studentized residuals having an absolute value higher than the one we consider outliers. The absolute value of the DFFITS limit is 0.04; any DFFITS absolute value higher than this limit will indicate that the outlier has a significant effect on the parameters of the curve fitting equation and should be removed. The maximum number of outliers is set equal to 2. Is the sample has more than two outliers, the sample will be set aside for review since it may be considered to be in error. Table 1 below displays the sensor output, Studentized residuals and DFFITS values for each update times in which the measurement was taken.

TABLE 1

| Time (s) | Log time | sensor output (mV) | Studentized Res. | DFFIT (delta55) |
|---|---|---|---|---|
| 15 | 1.176091 | −280.41814 | −0.167969237 | 0.02924 |
| 16 | 1.20412 | −280.55 | −0.584557754 | 0.07786 |
| 17 | 1.230449 | −280.38466 | −0.031943123 | 0.00324 |
| 18 | 1.255273 | −280.36149 | 0.048486072 | −0.00351 |
| 19 | 1.278754 | −280.34518 | 0.105178236 | −0.00484 |
| 20 | 1.30103 | −280.33188 | 0.151657918 | −0.00331 |
| 21 | 1.322219 | −280.30999 | 0.223545623 | 0.00016 |
| 22 | 1.342423 | −280.29411 | 0.277612041 | 0.00612 |
| 23 | 1.361728 | −280.27652 | 0.337580624 | 0.01431 |
| 24 | 1.380211 | −280.26493 | 0.380544209 | 0.02363 |
| 25 | 1.39794 | −280.24605 | 0.447273738 | 0.03632 |
| 26 | 1.414973 | −280.23704 | 0.485403754 | 0.04858 |
| 27 | 1.431364 | −280.22931 | 0.521192884 | 0.06190 |
| 28 | 1.447158 | −281.55 | −33.69556139 | −0.49856 |
| 29 | 1.462398 | −280.20571 | 0.625390089 | 0.09754 |
| 30 | 1.477121 | −280.18897 | 0.698680225 | 0.12198 |

As can be seen from Table 1, the Studentized residual at time 28 seconds has the maximum absolute value, −33.7, and the Studentized residual with the maximum absolute value is higher than the Studentized residual absolutely limit. The value at time 28 seconds is classified as an outlier. The DFFITS value for the Studentized residual with the maximum absolute value is 0.499 and is outside the DFFITS limit. The outlier is then removed. The outlier count is set to 1.

Figure 8B:
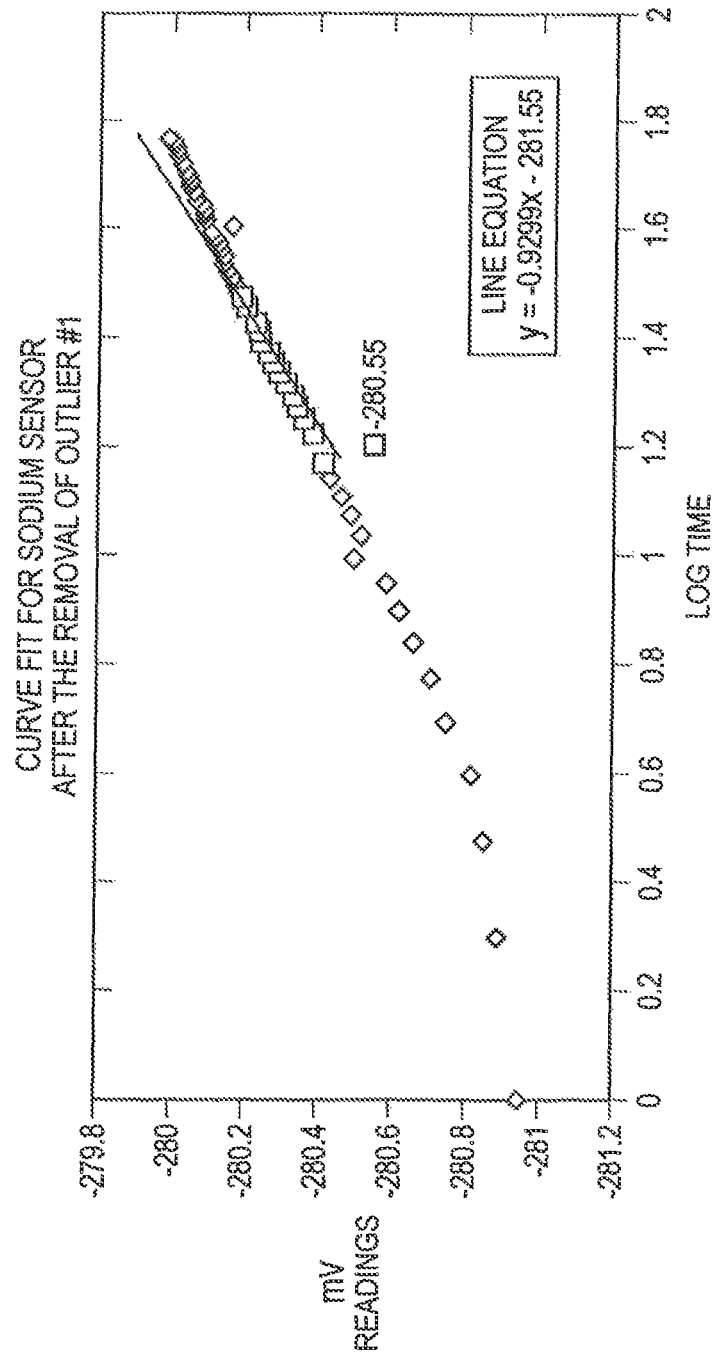

FIG. 8b shows the exemplary graphical representation of the data in FIG. 8a with the outlier at time 28 seconds removed. A curve fitting equation, of the type $ax^2+bx+c$ with a=0, is obtained from a curve fitting module 118 for the data set with the outlier at time 28 seconds removed. For the exemplary graphical representation shown there in the curve fitting equation is $0.9299x-281.55$. As can be seen from Table 2 below, the Studentized residual at time 16 seconds has the maximum absolute value, −38.7, and the Studentized residual with the maximum absolute value is higher than the Studentized residual absolutely limit. The value at time 16 seconds is classified as an outlier. The DFFITS value for the Studentized residual with the maximum absolute value is −0.5 and is outside the DFFITS limit. The outlier is then removed. The outlier count is set to 2.

TABLE 2

| Time (s) | Log time | sensor output (mV) | Studentized Res. | DFFIT (delta55) |
|---|---|---|---|---|
| 15 | 1.176091 | −280.41814 | 1.302207232 | −0.02519 |
| 16 | 1.20412 | −280.55 | −38.75323932 | 0.05453 |
| 17 | 1.230449 | −280.38466 | 0.659093643 | −0.00758 |
| 18 | 1.255273 | −280.36149 | 0.646980468 | −0.00515 |
| 19 | 1.278754 | −280.34518 | 0.480296708 | −0.00232 |
| 20 | 1.30103 | −280.33188 | 0.271488649 | −0.00051 |
| 21 | 1.322219 | −280.30999 | 0.329904217 | 0.00029 |
| 22 | 1.342423 | −280.29411 | 0.250562512 | 0.00088 |
| 23 | 1.361728 | −280.27652 | 0.241429866 | 0.00146 |
| 24 | 1.380211 | −280.26493 | 0.090161186 | 0.00077 |
| 25 | 1.39794 | −280.24605 | 0.156690447 | 0.00172 |
| 26 | 1.414973 | −280.23704 | −0.030955726 | −0.00041 |
| 27 | 1.431364 | −280.22931 | −0.242884222 | −0.00383 |
| 28 | 1.447158 | | | |
| 29 | 1.462398 | −280.20571 | −0.406073413 | −0.00749 |
| 30 | 1.477121 | −280.18897 | −0.322605674 | −0.00679 |

Figure 8C:
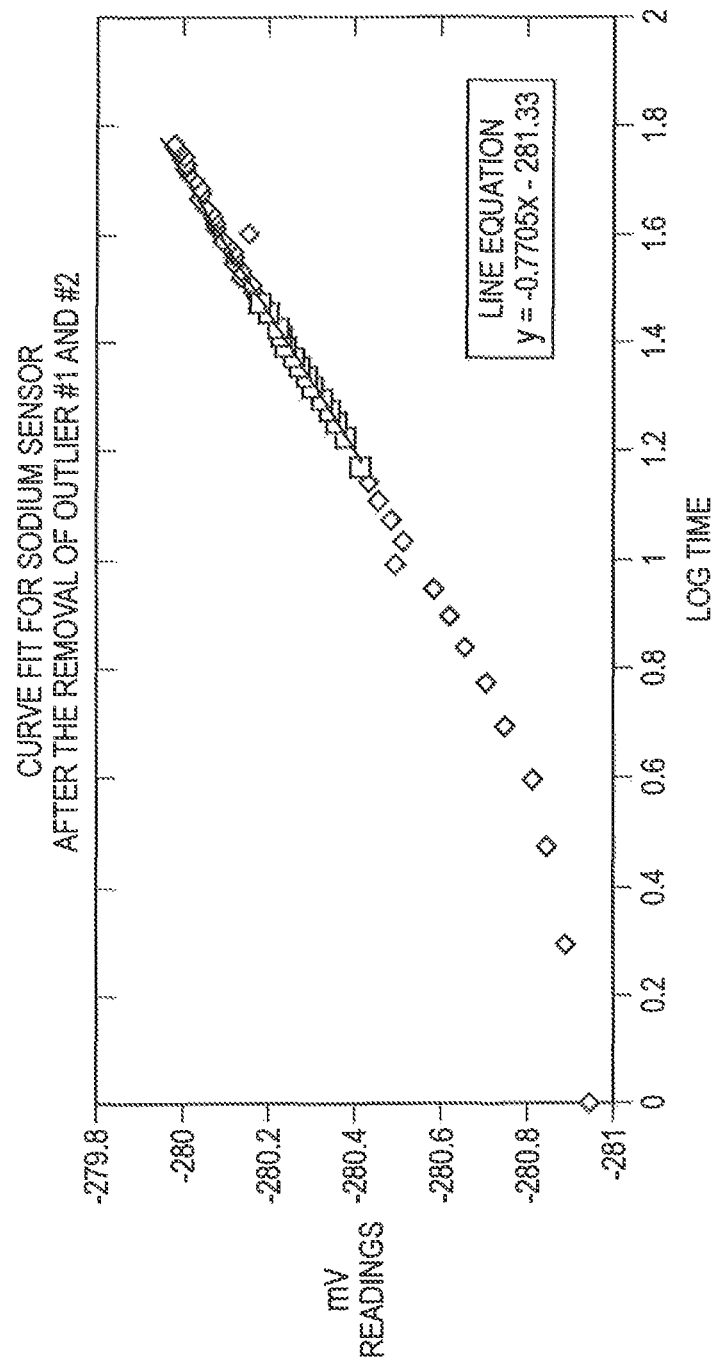

FIG. 8c shows the exemplary graphical representation of the data in FIG. 8a with the outlier at time 28 seconds removed and the outlier at time 16 seconds removed. A curve fitting equation, of the type $ax^2+bx+c$ with a=0, is obtained from a curve fitting module 118 for the data set with the outlier at time 28 seconds removed and the outlier at time 16 seconds removed. For the exemplary graphical representation shown there in the curve fitting equation is 0.7705x−281.33. As can be seen from Table 3 below, all the Studentized Residual values are within the limit and no DFFITS calculation are required. The outlier count is not higher than the outlier number limit.

TABLE 3

| Time (s) | Log time | sensor output (mV) | Studentized Res. | DFFIT (delta55) |
|---|---|---|---|---|
| 15 | 1.176091 | −280.41814 | −0.355455044 | not required |
| 16 | 1.20412 | | | not required |
| 17 | 1.230449 | −280.38466 | 0.170223356 | not required |
| 18 | 1.255273 | −280.36149 | −0.082739835 | not required |
| 19 | 1.278754 | −280.34518 | 0.02875639 | not required |
| 20 | 1.30103 | −280.33188 | 0.27049187 | not required |
| 21 | 1.322219 | −280.30999 | −0.077578419 | not required |
| 22 | 1.342423 | −280.29411 | −0.097178392 | not required |
| 23 | 1.361728 | −280.27652 | −0.267056658 | not required |
| 24 | 1.380211 | −280.26493 | −0.101176941 | not required |
| 25 | 1.39794 | −280.24605 | −0.427747325 | not required |
| 26 | 1.414973 | −280.23704 | −0.170357329 | not required |
| 27 | 1.431364 | −280.22931 | 0.136120199 | not required |
| 28 | 1.447158 | | | not required |
| 29 | 1.462398 | −280.20571 | 0.155631715 | not required |
| 30 | 1.477121 | −280.18897 | −0.181933585 | not required |

After the outlier detection is completed, each fit parameter from the last group of fit parameters, a=0, b=0.7705 and c=−281.33, is compared to the corresponding fit parameter limits. If any one of the parameters is outside the fit parameter limits for that parameter, the sample will be set aside for review since it may be considered to be in error. If all of the three parameters are within the corresponding fit parameter limit, extrapolation will take place and the results for the sample will be reported. For the exemplary embodiment shown in FIGS. 8a-8c, the fit parameter limits for parameter "b" are from 0.6 to 1.0 and the fit parameter limits for parameter "c" are from −290 to −260. Comparing each of the fit parameters from the last group of fit parameters, a=0, b=0.7705 and c=−281.33, to the fit parameter limits, each one of the each of the fit parameters from the last group of fit parameters is within the corresponding fit parameter limit. The sample value would be then reported. It should be noted that if the fit parameters from the first two groups of fit parameters had been compared to the corresponding fit parameter limits, they fit parameters would have been found to be outside of the fit parameter limits According to various embodiments, the disclosure presented herein may be utilized to reduce the time for determining an important response time of electrochemical sensors. In some embodiments, the electrochemical sensors may be used in a diffusion control response environment such as to calculate concentration levels of pO2, pCO2, glucose and lactate. In addition, the methodology may also be used for the end point detection of ion selective electrodes, such as and Na, K, Cl and Ca. Although some sensors typically exhibit fast responses and therefore an endpoint sensor response prediction may not be necessary, a curve fit may still be useful and the determination and improvement of the curve fit equation is still of importance.

What is claimed is:

1. A method for detecting a transient error in a body fluid sample taken from a patient, the method comprising:
   in a clinical analyzer, exposing a sensor to a body fluid sample containing an analyte for determining a concentration of the analyte in the body fluid sample, wherein the sensor generates a data signal in response to being exposed to the body fluid sample;
   generating a sample response curve representing the data signal;
   determining coefficients of an equation representing the sample response curve;
   comparing the coefficients of the equation representing the sample response curve to a predetermined range of coefficients, wherein the predetermined range of coefficients define a range of acceptable response curve shapes, the predetermined range of coefficients including coefficients of predetermined response curves corresponding to known concentrations of the analyte;
   detecting a transient error in the body fluid sample based on the comparison when the coefficients of the equation representing the sample curve are outside of the predetermined range of coefficients; and
   displaying a transient error notification in response to the transient error being detected.

2. The method of claim 1 wherein the equation representing the sample response curve is any one of logarithmic equation and quadratic equation.

3. The method of claim 1 wherein the comparing includes comparing a coefficient describing the curvature of the sample response curve to the range of coefficients and comparing a coefficient describing the slope of the sample response curve to a second range of coefficients different than the range of coefficients; and
   wherein the detecting includes detecting the transient error in the body fluid sample based on the comparison of the coefficient describing the curvature of the sample response curve and the comparison of the coefficient describing the slope of the sample response curve.

4. The method of claim 1 wherein the range of coefficients for a given concentration of analyte includes a mean coefficient determined from a mean of coefficients of the predetermined response curves corresponding to the given concentration of analyte;

a lower limit defined by a negative number of standard deviations from the mean coefficient; and an upper limit defined by a positive number of standard deviations from the mean coefficient.

5. The method of claim 4 wherein an absolute value of the negative number of standard deviations from the mean coefficient and an absolute value of the positive number of standard deviations from the mean coefficient are different.

6. The method of claim 4 wherein the lower limit and the upper limit of the range of coefficients are invariant to changes in concentration of the analyte.

7. The method of claim 4 wherein at least one of the lower limit and the upper limit of the range of coefficients varies with changes in concentration of the analyte.

8. The method of claim 4 further comprising revising the range of coefficients based on the coefficient of the sample response curve corresponding to the concentration of the analyte in the body fluid sample.

9. The method of claim 1 wherein the known concentrations of the analyte are determined from at least one of previously collected body fluid samples and standardized solutions.

10. The method of claim 1 wherein the range of coefficients depends on a matrix of the body fluid sample.

11. The method of claim 1 further comprising based on a result of the detection, determining the concentration of the analyte in the body fluid sample based on the equation.

12. The method of claim 1 further comprising determining the concentration of the analyte in the body fluid sample based the equation; and wherein detecting the transient error includes detecting the transient error in the determined concentration of the analyte based on the comparison.

13. The method of claim 1 further comprising based on the detection, reporting to a user of the analyzer that a transient error is detected in the body fluid sample.

14. The method of claim 13 wherein the reporting includes to providing a visual alarm, an audible alarm or a combination thereof to the user.

15. The method of claim 1 further comprising based on the detection, stopping a sample measurement process including determining the concentration of the analyte.

16. The method of claim 1 further comprising based on the detection, reporting to a user of the analyzer that the body fluid sample may be compromised by a transient error; and continuing a sample measurement process including determining the concentration of the analyte.

17. A system for detecting a transient error in a body fluid sample, the system comprising:

a sensor for determining the concentration of analyte in the body fluid sample, the sensor configured to generate a data signal in response to being exposed to the body fluid sample;

a transient error detector coupled to the sensor, the transient error detector configured to:

generate a sample response curve representing the data signal, determine coefficients of an equation representing the sample response curve, compare the coefficients of the equation representing the sample response curve to a predetermined range of coefficients, wherein the predetermined range of coefficients defines a range of acceptable response curve shapes, the predetermined range of coefficients including coefficients of predetermined response curves corresponding to known concentrations of the analyte and detect a transient error in the body fluid sample based on the comparison when the coefficients of the equation representing the sample response curve are outside of the predetermined range of coefficients; and a display coupled to the transient error detector, the display configured to display a transient error notification in response to the transient error being detected.

18. The system of claim 17 wherein the equation representing the sample response curve is any one of logarithmic equation and quadratic equation.

19. The system of claim 17 wherein the range of coefficients for a given concentration of analyte includes a mean coefficient determined from a mean of coefficients of the predetermined response curves corresponding to the given concentration of analyte;

a lower limit defined by a negative number of standard deviations from the mean coefficient; and an upper limit defined by a positive number of standard deviations from the mean coefficient.

\* \* \* \* \*